United States Patent [19]
John

[11] Patent Number: 6,096,950
[45] Date of Patent: *Aug. 1, 2000

[54] COTTON FIBER-SPECIFIC PROMOTERS

[75] Inventor: Maliyakal E. John, Middleton, Wis.

[73] Assignee: Monsanto Company, St. Louis, Mo.

[ * ] Notice: This patent is subject to a terminal disclaimer.

[21] Appl. No.: 08/749,522

[22] Filed: Nov. 18, 1996

Related U.S. Application Data

[63] Continuation-in-part of application No. 08/467,504, Jun. 6, 1995, and a continuation-in-part of application No. 08/298,829, Oct. 19, 1994, Pat. No. 5,620,882, which is a continuation of application No. 07/885,970, May 18, 1992, Pat. No. 5,495,070.

[51] Int. Cl.[7] .............................. A01H 5/00; C07H 21/04; C12N 15/82
[52] U.S. Cl. ...................... 800/314; 435/320.1; 536/24.1
[58] Field of Search ................................... 536/23.1, 24.1; 435/320.1, 172.3, 69.1, 419, 468; 800/205, DIG. 27, DIG. 63, 278, 287, 298, 314

[56] References Cited

PUBLICATIONS

Koziel MG, et al. "Optimizing expression of transgenes with an emphasis on post–transcriptional events." Plant Mol. Biol. 32: 393–405, 1996.

Mulrean EN. "Effect of Phymatotrichum root rot on yield and seed and lint quality in *Gossypium hirsutum* and *G. barbadense*." Plant Disease 68: 381–383, 1984.

*Primary Examiner*—Amy J. Nelson
*Attorney, Agent, or Firm*—Pharmacia Corporation; Timothy K. Ball; Dennis R. Hoerner, Jr.

[57] ABSTRACT

An isolated cotton fiber-specific promoter is disclosed. Preferably, this promoter comprises a nucleotide segment comprising at least 2.7 kb of the upstream genomic of a gene of the E6 family, or 1.7 kb of the upstream genomic family of the FbLate family.

6 Claims, 16 Drawing Sheets

COTTON FIBER-SPECIFIC PROMOTERS

CROSS-REFERENCE TO RELATED APPLICATION

This application is a continuation-in-part of U.S. Ser. Nos. 08/467,504 filed Jun. 6, 1995 and 08/298,829 filed Oct. 19, 1994, issued as U.S. Pat. No. 5,620,882, which is a continuation of Ser. No. 07/885,970, filed May 18, 1992, issued as as U.S. Pat. No. 5,495,070. All of these applications and patents are incorporated by reference as if fully set forth herein.

BACKGROUND OF THE INVENTION

Genetic Engineering of Plants

The hurdle of creating successful genetically engineered plants in major crop varieties is now being overcome sequentially on a plant-by-plant basis. While plant genetic engineering has been successfully demonstrated in several model plant species, most notably tobacco, carrot and petunia, these species are not considered agriculturally important. Therefore, researchers have directed their efforts toward improving commercially important crop plants through the use of genetic engineering (Potrykus, I., *Annu. Rev. Plant Physiol. Plant Mol. Biol.* 42:205–225, 1991).

The term "genetic engineering," as used herein, is meant to describe the manipulation of the genome of a plant, typically by the introduction of a foreign gene into the plant, or the modification of the genes of the plant, to increase or decrease the synthesis of gene products in the plant. Typically, genes are introduced into one or more plant cells which can be cultured into whole, sexually competent, viable plants which may be totally transformed or which may be chimeric, having some tissues transformed and some not. These plants can be self-pollinated or cross-pollinated with other plants of the same or compatible species so that the foreign gene or genes carried in the germ line can be bred into agriculturally useful plant varieties.

Current strategies directed toward the genetic engineering of plant lines typically involve two complementary processes. The first process involves the genetic transformation of one or more plant cells of a specifically characterized type. The term "transformation" as used herein means that a foreign gene, typically in the form of a genetic construction, is introduced into the genome of the individual plant cells. This introduction is typically through the aid of a vector, which is integrated into the genome of the plant. The second process then involves the regeneration of the transformed plant cells into whole sexually competent plants. Neither the transformation nor regeneration process need to be 100% successful, but must have a reasonable degree of reliability and reproducibility so that a reasonable percentage of the cells can be transformed and regenerated into whole plants.

Genetic Engineering of Cotton

Although successful transformation and regeneration techniques have been demonstrated in model plant species (Barton, et al., *Cell* 32:1033–1043 (1983), wherein the transformation and regeneration of tobacco plants was reported) similar results with cotton have only been achieved relatively recently. Umbeck, et al., *Bio/Technology* 5[3]:263–266 (1987); Firoozabady, et al., *Plant Mol. Bio.* 10:105–116 (1987); Finer, et al., *Plant Cell Rep.* 8:586–589, 1990; U.S. Pat. No. 5,004,863.

Successful transformation and regeneration of genetically engineered cotton plants has the potential to be of significant value to this agriculturally important crop. One of the most important benefits potentially achievable from genetically engineering cotton plants is the alteration and modification of cotton fiber quantity and quality.

Cotton Fiber

Cotton is one of the most important cash crops. Cotton fiber (seed hair) is a differentiated single epidermal cell of the ovule. At maturity the fiber cell consists of a cell lumen, primary cell-wall and secondary cell-wall. The primary cell-wall is made up of pectic compounds, cellulose, and small amounts of protein. The secondary cell-wall consists of cellulose. At maturity, the cotton fiber contains 87% cellulose.

Cotton fiber development can be divided into initiation, primary cell-wall synthesis, secondary cell-wall deposition, and maturation phases. Many hundreds of genes are required for the differentiation and development of cotton fiber. Work on in vitro translated fiber proteins (Delmer, et al., *J. Cell Sci. Suppl.* 2:33–50, 1985), and protein isolated from fiber (Graves and Stewart, *J. Exp. Bot.* 39:59–69, 1988) clearly suggests differential gene expression during various developmental stages of the cell. However, only a few of the genes involved in the biosynthesis of the large numbers of fiber-specific structural proteins, enzymes, polysaccharides, waxes or lignins have been identified (John and Crow, *Proc. Natl. Acad. Sci. USA* 89:5769–5773, 1992; John, *Plant Physiol.* 107:1477–1478, 1995). Since these genes and their interactions with environment determine the quality of fiber, their identification and characterization is considered to be an important aspect of cotton crop improvement.

The present invention is designed to approach fiber modification through genetic engineering. Such an endeavor requires fiber-specific promoters, genes that will modify fiber properties, and an efficient transformation technique.

The quality of the cotton fiber is dependent on such factors as the extent of elongation and degree of secondary wall deposition. It is assumed that a number of genes as well as environmental factors regulate the physical characteristics of the fiber, such as length, strength and micronaire value. However, the genes responsible for cellulose synthesis and fiber development in cotton plants are heretofore generally uncharacterized at a molecular level.

The most commercially useful plant fiber is derived from cotton (*Gossypium arboreum, Gossypium herbaceum, Gossypium barbadense*, and *Gossypium hirsutum*). However, there are other fiber-producing plants. These plants include the silk cotton tree (Kapok, *Ceiba pentandra*), desert willow, creosote bush, winterfat, balsa, rami, kenaf, hemp, roselle, jute, sisal abaca and flax.

Promoters

Promoters are DNA elements that direct the transcription of RNA in cells. Together with other regulatory elements that specify tissue and temporal specificity of gene expression, promoters control the development of organisms. Thus, there has been a concerted effort in identifying and isolating promoters from a wide variety of plants and animals.

Many promoters function properly in heterologous systems. For example, plant gene promoters such as rbcS, Cab, chalcone synthase and protease inhibitor from tobacco and Arabidopsis are functional in heterologous transgenic plants. (Reviewed by Denfey, et al., *Science* 244:174–181, 1989). Specific examples of transgenic plants include tissue-specific and developmentally regulated expression of soybean 7s seed storage protein gene in transgenic tobacco plants (Chen, et al., *EMBO J.* 7:297–302, 1988) and light-dependent organ-specific expression of *Arabidopsis* thaliana chlorophyll a/b binding protein gene promoter in transgenic tobacco (Ha and An, *Proc. Natl. Acad. Sci. USA* 85:8017–8021, 1988). Similarly, anaerobically inducible maize sucrose synthase-1 promoter activity was demonstrated in transgenic tobacco (Yang and Russell, *Proc. Natl. Acad. Sci. USA* 87:4144–4148, 1990). Tomato pollen promoters were found to direct tissue-specific and developmentally regulated gene expression in transgenic Arabidopsis and tobacco (Twell, et al., *Development* 109:705–713, 1990). Thus, some plant promoters can be utilized to express foreign proteins in plant tissues in a developmentally regulated fashion.

BRIEF SUMMARY OF THE INVENTION

Our objective in the work described below is to disclose the minimum length of various cotton promoters necessary to direct tissue and developmental specificity of gene expression and to disclose where tissue and developmental regulatory regions are located within the promoter. In the Examples below, we have demonstrated that a 2.7 kb fragment from the upstream region beginning from the putative initiation codon (ATG) of one E6 gene is necessary for preserving tissue-specific expression of heterologous transgenes in transgenic cotton. We have further demonstrated that there are several members of the E6 gene family in cotton. For example, there are two homologous E6 genes identified from Coker 312 and two from Sea Island cotton varieties (John, *Plant. Mol. Biol.* 30:297–306, 1996). Based on the nucleotide sequence identities of these E6 genes we further envision that other E6 promoters will behave in a similar fashion with regard to tissue and developmental specificity. Furthermore, E6 genes from Kapok have been isolated and shown that they, too, are homologous to cotton genes. Thus, we also envision that the upstream region of Kapok E6 gene is also likely to contain DNA elements necessary for correct tissue-specific expression.

Another cotton promoter, from the FbLate gene family, was also isolated and shown to be active in transgenic cotton. We demonstrated that at least a 1.7 kb promoter fragment from the putative initiation codon of FbLate2 gene is necessary to preserve tissue specificity of transgene expression in transgenic cotton.

Furthermore, we envision that tissue-specific elements are situated upstream of 1.1 kb from the putative initiation codon of promoter fragment of B8 gene and that this region is necessary for correct tissue-specific expression of transgenes in transgenic cotton.

Therefore, the present invention is a fiber-specific promoter comprising a nucleotide segment comprising at least 2.7 kb of the upstream genomic sequence of an E6 gene. In a preferred form of the invention, the E6 gene is selected from the group consisting of the E6-1A, E6-4A, E6-3B, E6-2A, and CPE6-1A (from Kapok) members of the E6 gene family.

In an especially preferred form of the invention, the fiber-specific promoter comprises SEQ ID NOs:1, 2, 3 or 4.

In another embodiment, the present invention is a fiber-specific promoter comprising a nucleotide sequence comprising at least 1.7 kb of the upstream genomic sequence of an FbLate gene. In a preferred form of the invention, the FbLate gene is FbLate2. In an especially preferred form of the invention, the fiber-specific promoter comprises 1.7 kb of the initial upstream region of SEQ ID NO:5.

In another embodiment, the present invention is fiber-specific promoter comprising a nucleotide sequence comprising at least 2.2 kb of the upstream genomic sequence of a B8 gene. In an especially preferred form of the invention, the fiber-specific promoter comprises SEQ ID NO:6.

In another preferred form of the present invention, the fiber-specific promoter is operably connected to a protein-encoding DNA sequence, wherein the protein-encoding DNA sequence is not natively connected to the promoter. The present invention is also a method of creating a transgenic fiber producing plant, preferably cotton, comprising the fiber-specific promoter operably connected to the protein-encoding sequence. The present invention is also a transgenic plant, cell, or seed comprising the construct.

It is an object of the present invention to provide a tissue-specific promoter and method of creating a transgenic fiber-producing plant.

It is another object of the present invention to provide an improved, shortened fiber-specific promoter.

Other objects, features and advances of the present invention will become apparent after examination of the specification, claims and drawings.

DETAILED DESCRIPTION OF THE INVENTION

Figure 1:
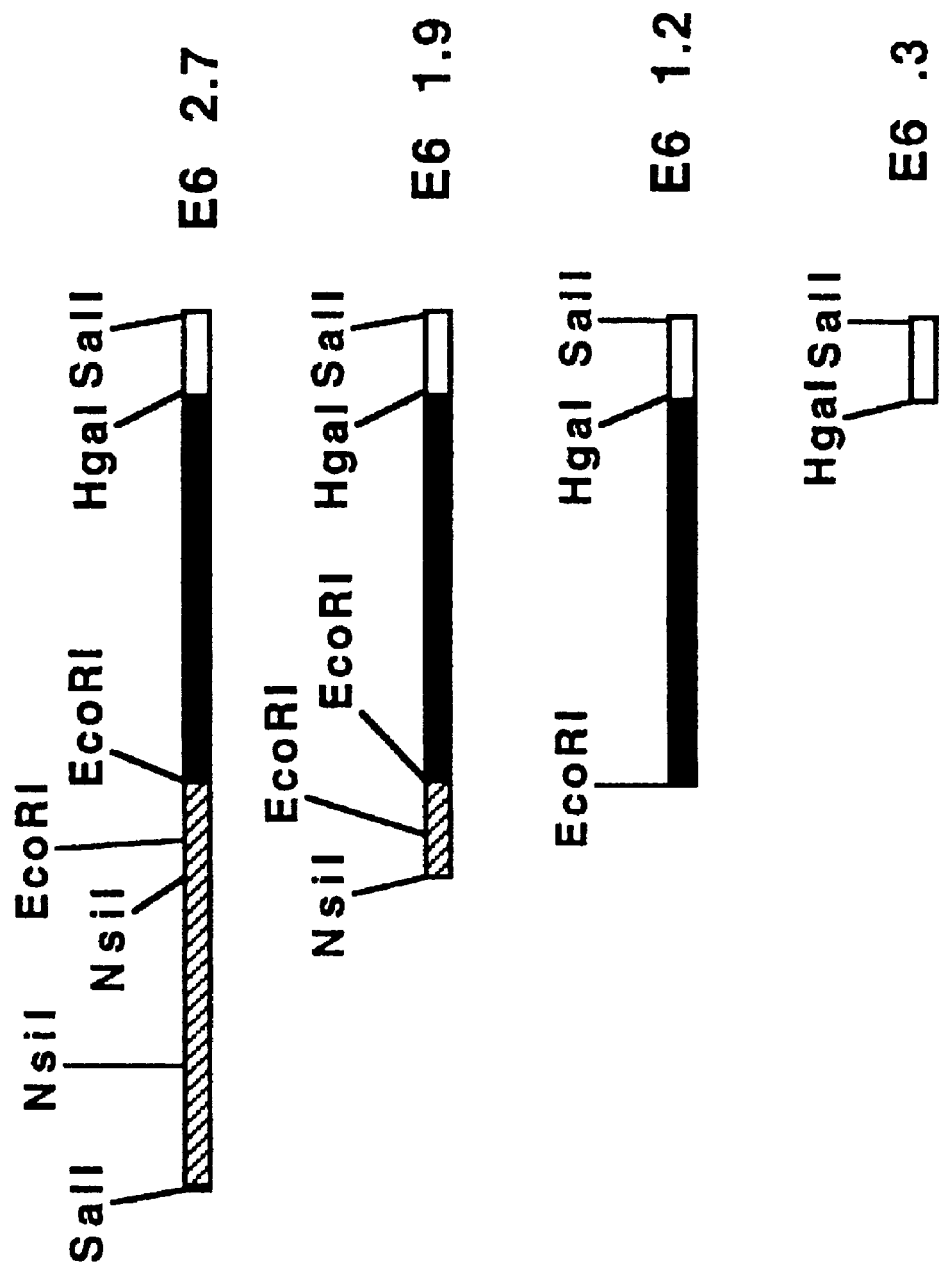
FIG. 1 is a restriction map of deletions made in the E6-3B promoter.

In many instances, it is desirable for a transgene to be developmentally regulated so as to be expressed only in fiber cells at a proper developmental stage. This regulation can be most expeditiously accomplished by a promoter capable of preferential promotion. We are interested in expressing transgenes with promoters that are active during both fiber development in general and in late fiber development. We term a promoter active in late fiber development an "FbLate" promoter.

The present invention is a gene construct comprising a fiber-specific promoter or an FbLate promoter and a method of creating transgenic fiber-producing plants, plant cells and seeds. Therefore, the method first involves identifying promoters that preferentially promote gene expression in fiber cells during both fiber development and during late fiber development (20 days post anthesis). (By "preferentially promote" we mean that the gene is either expressed only during fiber development in fiber cells or is expressed more actively in fiber cells than it is expressed in other plant tissue cells.)

In one embodiment, the present invention is an isolated fiber-specific promoter comprising a nucleotide segment comprising at least 2.7 kb of the upstream genomic region of a gene of the E6 family or 1.7 kb of the upstream region of a gene of the FbLate. By "upstream genomic region" we mean the region immediately upstream from the translation initiation site.

Our Examples below have demonstrated that these 2.7 kb and 1.7 kb upstream genomic regions are necessary for tissue-specific expression.

In a particularly advantageous form of the present invention the 2.7 kb E6 promoters would comprise SEQ ID NOs:1–4 and the FbLate promoter would comprise the initial 1.7 kb upstream region of SEQ ID NO:5. In the description below, we describe various truncations, deletions, and substitutions that are also part of the present invention.

We have identified five promoters from the E6 gene family and one promoter from the FbLate2 gene family. However, we envision that both of these families have many other members and one might wish to isolated a promoter from another family member. One way to identify suitable promoters is by isolating mRNA from fiber-producing cells, making a complementary DNA (cDNA) library of cDNA clones from the mRNA, and screening the cDNA library with cDNA generated from other tissues to identify and eliminate RNAs which are expressed in tissues other than those which produce fiber. This screening procedure will result in the identification of cDNA clones that are expressed preferentially in fiber cells. A similar process may be used to determine which cDNA clones encode RNA molecules that are prevalent in late fiber development.

After the identification process is complete, the fiber-specific cDNA clones may be used to screen genomic clones created from the DNA of fiber-producing plants. This screening process results in the selection of genomic clones with sequences homologous to the fiber-specific cDNAs. Because a fiber-specific promoter will be upstream from a sequence that is expressed specifically during fiber development in a fiber cell, the promoter sequence may be identified on this genomic clone. These promoter sequences may be excised and attached to genes which if expressed in fiber cells would alter fiber quality or quantity. (Although the plant may be any of a number of varieties of fiber-producing plants, cotton, e.g., Gossypium plants, are the preferred plants for purpose of the present invention.)

To determine the sequences within a gene necessary for fiber-specific expression, nucleotide sequences of the coding region and regions flanking the coding region can be subjected to computer analysis to identify sequence patterns that correspond to consensus regulatory elements. Potential regulatory elements are usually present at the 5' flanking region of the gene, 30 to 100 bases upstream from the transcription start site in eukaryotic genes (for reviews see Breathnach and Chambon, *Annu. Rev. Biochem.* 50:349–383, 1981; Johnson and McKnight, *Annu. Rev. Biochem.* 58:799–839, 1989). In addition to the promoter (TATA box) other consensus sequences such as the CATC box and the CACA box, may also be present in specific groups of genes. Messing, J., et al., in Genetic *Engineering of Plants, an Agricultural Perspective*, Kosuge, et al. eds. pp. 211–227 (1983); Forde, B. G., et al., *Nucl. Acid Res.* 13:7327–7339 (1985); Goldberg, R. B., *Philos. Trans. Roy Sci. B*314:343–354 (1986). A search of the 5' flanking sequences of the gene can identify these sequence patterns.

The present invention is preferably performed with a cotton genomic DNA fragments that we have identified as containing fiber-specific promoter activity.

If one wishes to recreate the fiber-specific promoter, one could first screen a cotton genomic library with a probe prepared from SEQ ID NOs:1–6. One of skill in the art of molecular biology would be able to select a probe from this sequence and screen a cotton genomic library to obtain homologous sequences. These sequences could then be analyzed for the presence of the fiber-specific promoter sequence.

A sequence that is a variation of nucleotides SEQ ID NOs:1–6 may also contain fiber-specific promoter activity because it is not necessary for a DNA fragment to contain an identical nucleotide sequence to be functionally identical to the promoter sequences described herein. The sequence must only be sufficiently homologous to SEQ ID NOs:1–6 or to the initial 2.7 kb upstream regions of the E6 gene family, the 1.7 kb upstream region of the FbLate gene family or the initial 2.2 kb upstream region of the B8 gene family to retain promoter activity. Some nucleotide deletions, additions, and replacements, either naturally occurring or artificially induced, may have only a minor impact on gene expression.

A preferable sequence suitable as a fiber-specific promoter would comprise a sequence at least 50% to 80% homologous to SEQ ID NOs:1–6 or the 2.7 kb upstream region of the E6 gene family, the 1.7 kb upstream region of the FbLate family or the 2.2 kb upstream region of the B8 family. We refer to such a substituted promoter as a "functional equivalent." A functional equivalent retains at least 50% to 80% nucleotide sequence homology and has an equivalent fiber specificity as the promoters described below. One of skill in the art can compare a candidate "functionally equivalent promoter" with those described below to determine whether the candidate promoter is suitable for the present invention.

The promoter fragment described herein may be further truncated to determine the absolute smallest fragment capable of tissue-specific and development-specific expression. We refer to such a modification as a "functional deletion variation." Methods of truncating a clone include deleting sequences and digesting the clone with a restriction enzyme or other nuclease. These methods are commonly known in the art of molecular biology. Preferably, these truncations will take place at the 5' region of a 2.7 kb promoter fragment (for the E6 gene family), a 1.7 kb promoter fragment (for the FbLate gene family) or a 2.2 kb promoter fragment (for the B8 gene family).

A suitable "functional deletion variation" of and 2.7 kb nucleotide segment of the upstream region of a gene of the E6 family comprising SEQ ID NOs:1–4 or the initial 1.7 kb upstream region of SEQ ID NO:5 will have the same fiber-specific promoter properties as the promoters described below. The description below demonstrate these properties.

One may use a transient reporter gene expression system to assess promoter activity of candidate promoter fragments.

In such an assay, the fragment to be assayed would be linked to a reporter gene and used to transform a plant cell. Useful reporter genes include chloramphenicol acetyltransferase (CAT), luciferase (Lux), and β-glucuronidase (GUS). Alam and Cook, *Anal. Biochem.* 188:245–254, 1990; Jefferson, *Plant Mol. Biol. Rep.* 5:387–405, 1987. We have described a reporter gene assay below.

Further confirmation of the promoter activity and tissue-specific and developmental expression can be obtained by stably integrating a chimeric construct comprised of the DNA segment and reporter gene into plants and following the reporter gene's expression through development. The Examples below describe a typical method of examining the expression of specific RNA species.

Another way to obtain a sequence capable of preferentially promoting expression in fiber-producing plants is to probe a library of DNA obtained from a fiber-producing plant with a probe prepared from SEQ ID NOs:2–29 of U.S. Pat. No. 5,521,078, hereby incorporated by reference.

The DNA probe does not have to encompass the entire sequence and only need be of a length sufficient to hybridize specifically to a suitable clone. If a sequence from a fiber-specific cDNA clone is used, one will isolate the genomic clone homologous to that cDNA. Because promoter sequences are found upstream from the sequences homologous to the cDNA clone, one must examine these upstream sequences to find the promoter. Analysis of the upstream sequence, as described above, will delineate which part of the sequence is needed for promoter activity.

After a fiber-specific promoter has been identified and isolated, the promoter must be placed upstream of a protein-encoding gene whose expression is desired. By "protein-encoding sequence" we mean a sequence that encodes at least a portion of a protein and is either in the sense or antisense orientation. By "expressed" we mean to include DNA sequences expressed as RNA or as protein. Preferably, the product of this gene is capable of altering fiber quality or quantity. Conventional molecular biological techniques may be used to create suitable constructs.

These constructs must be transformed into a cotton plant or cell. Stable integration and expression of foreign genes in cotton plants has been demonstrated and repeated. Umbeck, et al., *Bio/Technology* 5[3]:263–266 (1987); Firoozbady, et al., *Plant Mol. Biol.* 10:105–116 (1987). Using the techniques taught in these papers, the transformation of cotton tissues is accomplished by Agrobacterium infection and regeneration. Although a lengthy process, the Agrobacterium-mediated transformation of cotton has also been practiced by other laboratories and can now readily be replicated by those of ordinary skill in plant genetic engineering.

It is to be understood, however, that other methods for the transformation of cotton plants and lines are being studied, and that the transgenic cotton plants and lines with fiber genes introduced into them will prove advantageous and useful regardless of the method of transformation of the original tissues. Specifically, it has now been demonstrated that higher plants can be stably genetically transformed by particle-mediated transformation techniques, which avoid many of the difficulties and delays inherent in plant regeneration required by Agrobacterium plant transformation. McCabe, et al., *Bio/Technology* 6[8]:923–926 (1988). Recent research results suggest that routine particle-mediated transformation of cotton is to be expected shortly. McCabe and Martinelli, *Bio/Technology* 11:596–598 (1993).

The present invention is a useful genetic engineering tool for the introduction of altered fiber-specific characteristics into cotton plants. The identification and introduction of fiber-specific promoters from one cotton plant variety to another can be extended to include other exotic plants that produce fiber. Many of these plants will have fiber-specific promoters with one or more desirable qualities, which can be incorporated into a cotton plant.

The promoters of the present invention can be utilized in modulating the synthesis of fiber proteins or to introduce non-fiber proteins into fiber in a tissue-specific and development-specific manner.

Another approach to creating cotton plants with altered fiber characteristics is to create antisense genetic constructs with fiber-specific promoters to inhibit or induce the expression of one or more fiber genes in fiber cells. The theory behind antisense genetic constructs is that the production of RNA strands in the cells of an organism which are complementary to the mRNA of an endogenous gene will result in hybridization of the antisense RNA to the native mRNA resulting in decreased expression of the mRNA gene.

Smith, et al., *Nature* 334:724–726, 1988; Bird, et al., *Bio/Technology* 9:635–639, 1991; Van der Krol, et al., *Gene* 72:45–50, 1988. Thus, in an antisense construct, a complete coding sequence for the mRNA is not needed. All that is needed is a sequence of sufficient length to construct a selectively hybridizing antisense RNA.

The following Examples are a description of the process and materials used to identify truncated fiber-specific promoters and to use the promoter to transform cotton plants. Although reference to cotton is specifically made, it is within the scope of the present invention to substitute other fiber-producing plants.

EXAMPLES

In General

Examples 1–2 describe the creation and analysis of fiber-specific cDNAs. Examples 3–13 describe the creation and analysis of fiber-specific cDNAs and promoters. Example 14 describes the creation and analysis of truncated fiber-specific promoters.

1. Isolation of RNA From Fiber

Fiber cells at different stages of development from fiber-producing plants were collected and quick-frozen in liquid nitrogen. Specifically, fiber cells from 15 and 23- day-old Coker 312 or 10-day-old Sea Island bolls were collected and quick-frozen. The frozen fiber cells were then powdered in a mortar in liquid nitrogen and homogenized in a homogenization buffer for 1.5 minutes using a polytron at full speed. The homogenization buffer included the following ingredients: 5 M Guanidine isothiocyanate; 0.2 M Tris-acetate (pH 8.5); 0.7% Beta-mercaptoethanol; 1% polyvinyl pyrrolidone (PVP, MW 40 Kd), and 0.62% sodium lauroyl sarcosine. Beta-mercaptoethanol and PVP were added just before use. A ratio of 1:2 of tissue (weight) to buffer (volume) was used.

The homogenate was filtered through Mira cloth and layered over a 1.5 ml pad of 5.7 M cesium chloride as described by Chirgwin, J. M., et al., *Biochemistry* 18:5294–5299 (1979). The homogenate was then centrifuged for 18 hours at 36,000 rpm in a SW 50.1 rotor at 20° C. After centrifugation, the RNA was collected as described by Chirgwin, et al. (supra).

The RNA was then further purified by phenol:chloroform extractions and precipitations in the presence of ammonium acetate as described for DNA by Crouse, et al., *Focus* 9[2]:3–5 (1987). Poly(A)+RNA was obtained by oligo-(dT)

chromatography as described by Maniatis, et al., in *Molecular Cloning: A Laboratory Manual*, Cold Spring Harbor Laboratory, Cold Spring Harbor, N.Y., (1982).

2. Library Construction and cDNA Clone Identification

Complementary DNA (cDNA) libraries were prepared from the mRNA according to the protocol developed by D'Alessio, et al., *Focus*, 9[1]:1–4 (1987) with the following exceptions: The first strand of cDNA was synthesized using a primer having the following sequence dATGCTGGTACC(T)$_{15}$ (SEQ ID NO:10 in U.S. Ser. No. 08/467,504); the second strand synthesis was carried out as described by D'Alessio, et al., supra, for tailing. The poly-(dC) tails were added to the double-stranded cDNA and then annealed to poly-(dG)-tailed psR322 plasmid vector (Bethesda Research Laboratories). The recombinant plasmids were used to transform *Escherichia coli* (*E. coli*) RR1 strain as described by Hanahan in *DNA Cloning a Practical Approach, Vol. 1* (1985) pp. 109–135. The transformed cells were selected on agar plates containing the antibiotic tetracycline (12 mg/liter).

Separate cDNA libraries were constructed from the mRNAs from 10-day, 15-day, and 23-day-old fiber cells. For the 10-day fiber cell mRNAs, an oligo-(dT) primer was used for cDNA synthesis instead of the primer described above. The 10-day cells were selected to be representative of genes active during the primary cell wall stage of cell development. In the 15-day-old cell, both primary cell wall and secondary cell wall synthesis systems are active. The 23-day-old cells were selected to be representative of genes active principally during secondary wall synthesis.

The clones in the library were then transferred to nitrocellulose filters and duplicate filters were made according to Hanahan, et al., *Gene* 10:63–67 (1980). About 25,000 clones from the 15-day and 23-day libraries were screened using the following procedure. $^{32}$P-labelled single-stranded cDNA probes were prepared from poly(A)+RNAs using $^{32}$P-dCTP and reverse transcriptase as described by Maniatis, et al., supra. Probes were prepared from poly(A)+RNAs of 15-day, 23-day old fiber producing cells, and from 0-day ovule, leaf, root and flower cells. Prewashings, prehybridizations, hybridizations and washings of the filters were performed as described in detail in John, et al., *Proc. Natl. Acad. Sci. USA* 81:5628–5632 (1984).

The autographic signals from filters hybridized with $^{32}$P-labelled cDNAs from the different tissues were then compared. The clones which hybridized to cDNAs from fiber producing cells, but not to cDNAs from other tissues, were selected. The resulting clones were then subjected to a second cycle of differential screening as described above and additional clones were eliminated as non-fiber specific. This process was continued for a third and then a fourth time. This repetitive screening was to eliminate clones which showed hybridization to other than cDNAs from fiber producing cells.

The final collection of clones were then subjected to northern analysis. For this analysis, poly(A)+RNA from different tissues were denatured in the presence of formaldehyde and size-fractionated on 1.5% agar/formaldehyde gels as described by John, et al., supra. The RNAs were then blotted to nitrocellulose and probed with $^{32}$P-labelled inserts of each individual clone. The clones that showed hybridization to only RNAs from fiber cells were selected. This screen resulted in the identification of cDNAs specific to five fiber specific genes. All manipulations on plasmid DNAs such as isolation, purification on cesium chloride gradients, restriction digestion, insert purifications by gel electrophoresis and electroelutions and $^{32}$P-labelling by nick-translations have been described previously (Maniatis, et al., supra and John, et al., supra).

The cDNA library from the 10-day old cells was then screened using a subtractive hybridization procedure as follows. The $^{32}$P-labelled cDNA from fiber was hybridized to excess biotinylated mRNA isolated from leaf tissue. The cDNA-biotinylated mRNA hybrids and the excess biotinylated mRNAs were separated from unhybridized cDNA by extraction with avidin in phenol:chloroform. The streptavidin was partitioned into the organic phase along with any biotinylated nucleic acid while the single-stranded cDNA remained in the aqueous phase. This procedure has been described elsewhere, Duguid, et al., *Proc. Natl. Acad. Sci. USA* 85:5738–5742 (1988).

Subtractive hybridization screening of 4788 clones of the 10-day cell library with leaf cDNAs resulted in 800 clones not present in the leaf. These clones were then screened by cDNAs generated from ovule, flower and root mRNAs. The results of this screening were 79 putative fiber-specific clones. The duplicate clones which hybridized to each other were detected by the procedure of polymerase chain reaction (PCR) (Saiki, et al., *Science* 239:487–491, 1988), Southern blotting and hybridization. The PCR reaction was carried out by first mixing 10 microliters of bacterial culture of the cDNA clone added to 90 microliters of distilled water. 20 microliters of that mixture was added to a PCR reaction buffer of 50 mM KCl, 10 mM Tris-HCl pH 8.0, 2.5 mM MgCl$_2$, 0.01% gelatin, 200 µM each of dATP, dCTP, dTTP and dGTP, 12.5 picomolar each of sense and antisense primers for pBR322, and 0.5 units of Taq polymerase. The final reaction volume was 52 microliters. The PCR reactions were carried out in a Perkin-Elmer-Cetus thermocycler.

The amplified DNA from the PCR reactions was separated by agarose gel electrophoresis and blotted onto nitrocellulose by the method of Southern, *J. Mol. Biol.* 98:503–517 (1975). One or more bacterial clones from the same group was amplified by the same procedure and the products also separated on agarose gel. The amplified insert DNAs were then excised from the gel and purified by electroelution. The purified DNAs, labelled with $^{32}$P by nick-translation, were hybridized with the Southern blot. Thus, the cross-hybridizing clones were identified in this fashion.

This procedure resulted in the identification of 19 putative fiber-specific clones. The clones were further analyzed by northern blots. Three of the clones were found to be fiber-specific. Another five of the clones were found to be differentially expressed to a higher degree in fiber and to a lesser degree in other tissues. Fiber-specific cDNA clones were then used as probes to screen genomic libraries and isolated cross-hybridizing genomic clones.

3. Characterization of Fiber-Specific cDNA Clones

In the following sections, we describe each of the fiber cDNAs, their corresponding genes and their promoters. The nomenclature is as follows: CK=Coker, SI=Sea Island; FB15, FB10=15 or 10-day-old bolls; the last remaining letters and numbers signify the individual cDNA isolate.

CKFB15A1-E6 cDNA clone (E6 cDNA)

This cDNA clone for a fiber gene has an insert of 983 base pairs which hybridized to 1.0 and 1.1 Kb RNAs. The RNA is expressed in fiber and not in root. Flower leaf and ovule RNAs show weak hybridization.

The E6 RNA was found to be developmentally regulated. Its steady-state concentration increases immediately after anthesis. Our quantification of E6 transcript in fiber using in vitro synthesized E6 RNA as a control, shows that 20 μg of RNA from 20-day-old fiber contains about 3.5 ng of E6 RNA. Thus, E6 RNA is an abundant fiber RNA.

Hybrid selection translation experiments showed that E6 codes for two polypeptides of 26 and 30 kD. The E6 clone cross-hybridizes with Pima and Naked seed cotton fiber cell RNAs. The clone also cross-hybridizes with DNAs of a number of plants belonging to Gossypium species. Thus, DNAs from Pima and Sea Island (*G. barbadense*) PD3 and DP50 (*G. hirsutum*) and plants belonging to *G. longicalyx* and *G. somalense* all showed hybridization. In addition, plants belonging to another species of family Malvaceae, the Hibiscus are also found to have conserved E6 gene. DNAs of *H. sabdariffa* L. cv., Rosselle, Kapok (*Ceiba pentandra*) belonging to family Bombacaceae, Hemp (*Cannabis sativa*) belonging to family Moraceae also showed hybridization to E6 gene. We also confirmed that E6 or a homologous gene is present in *Gossypium darwinii, Gossypium herbaceum* L. cv. Jayadhar and Tzuyung, *Gossypium anomalum, G. australe, G. nelsonii, G. arboreim* L., cv., Nanking and Liaochung, *G. thurberi, G. davidsonii, G. raimondii, G. stocksii, G. somalense, G. longicalyx,* and *F. bickii.* Thus, the E6 sequence is conserved in most of the plants belonging to family Malvaceae and also found in two other families Bombacaceae and Moraceae. Many of these plants produce seed hair or bast fiber. Interestingly, we did not detect E6 hybridization in the DNAs of soybean, corn, tobacco or the cellulose producing bacterium Acetobacter (*A. xylinum*). These studies imply that E6 gene may have functions in the formation of seed hair or bast fiber cells.

The complete nucleotide sequence of E6 insert is presented as SEQ ID NO:2 of U.S. Pat. No. 5,495,070. This sequence contains a long open reading frame extending from position 1 to position 748. On this same open reading frame, start codons appear at positions 34, 61 and 94. If the first codon is the initiation site for the protein, the 714 nucleotide reading frame would yield a 238 amino acid protein. E6 cDNA clone was deposited with ATCC at Accession Number 67809.

SEQ ID NO:2 of U.S. Pat. No. 5,495,070 also contains an additional 84 residues and a stretch of poly(A) that originate from clone PCKFB15-B3. This clone is identical to pCKFB15A1-E6 except for the presence of additional residues at the 3'-end.

CKFb15A1-B8 cDNA clone (B8 cDNA) is also described in U.S. Pat. No. 5,495,070.

4. Characterization of FbLate-Specific cDNA clones

A 23-day fiber cDNA library was screened with cDNA from 24-day fiber poly(A) RNA. The first screen resulted in the identification of 573 hybridizing clones. The procedure was repeated with cDNAs from 23- and 10-day fiber poly (A) RNAs and resulted in the selection of 132 clones that showed strong hybridization to 23-day probe, but weak hybridization to 10-day probe. These clones were then subjected to cross hybridization to eliminate duplicate ones. Subsequently we hybridized the clones to 19 fiber specific cDNA clones identified from previous cDNA library screens (described above) to eliminate any previously identified clones. These 19 clones are described in U.S. Ser. No. 08/138,814 filed Oct. 18, 1993, M. John, (which is incorporated by reference). The cross-hybridizations eliminated a number of clones, and we selected 7 clones, (A8; A11; G4; G6; B2; C3; and F1) for further study.

Three of these clones (A8, A11 and G6) were then subjected to northern blot analyses to assess their expression patterns during development of the fiber. A8 and A11 clones strongly hybridized to 24-day fiber RNA while hybridization was weak or absent from 10-day fiber RNAs. Plasmid G6 hybridized to 24-day as well as 10-day fiber RNAs and also to leaf RNA.

The insert of A8 was sequenced and contains 974 bp (SEQ ID NO:1 of U.S. Ser. No. 08/138,814). The 645 bp insert of clone A11 was sequenced and is described at SEQ ID NO:2. This clone will be referred to as FbLate-2. We refer to clone A8 as FbLate-1. The nucleotide sequences of FbLate-1 and FbLate-2 were compared using the Bestfit computer program of Genetics Computer Group Inc. (GCG) Madison. The sequences showed a 90% similarity, suggesting that these two mRNAs are members of one gene family. The longest open reading frame in FbLate-l cDNA is 621 bases while FbLate-2 had an open reading frame of 425 bases.

Subcloning of these genomic DNA inserts into plasmid or phagemid vectors was done using standard protocols. Ligated DNAs were transformed into *Escherichia coli* strain XL-1 Blue (Stratagene). Recombinant clones were selected on the basis of blue/white selection on X-gal, IPTG (5-bromo-4-chloro-3-indoyl-beta-D-galactophyranoside; ispropyl-beta-thio-galactophyranoside) plates. The plasmid sizes of the recombinant clones were then analyzed by SDS-agarose gel electrophoresis (Sekar, V., *Biotechniques*, 5:11–13, (1987)). The inserts of the clones were further characterized by restriction mapping and Southern analysis. *Current Protocols in Molecular Biology*, (supra). If necessary, further subcloning of smaller restriction fragments that contain the cDNA hybridizing regions was also undertaken. The above protocols enable one to determine the approximate boundaries of a given gene.

The nucleotide sequence of the gene and the corresponding cDNAs were analyzed by computer programs to determine, among other things, the tentative coding region, presence of introns and exons, 5' and 3' non-coding regions and putative promoter regions. The software that we have used for this purpose is that of Genetics Computer Group (GCG), Madison. Once the detailed sequence analysis was performed and various putative structural components of the gene were identified, we were able to confirm these findings by various experiments. For example, we used a chimeric marker gene construct that includes the promoter fragment to transform a test cell. By observing the presence or absence of the marker gene activity, one can analyze the promoter function of that DNA fragment.

5. Characterization of genomic clones

Once the genomic clones were identified, they were subcloned into plasmid or phagemid vectors for easy manipulation, as discussed above. A schematic representation of the promoter fragments that we characterized is given in FIG. 1 of U.S. Pat. No. 5,495,070.

The nomenclature is as follows: EMBL and DASH= Lambda vector; SI=Sea Island, CK=Coker; CP=*Ceiba pentandra*; next to last two characters=the cDNA clone that hybridized to the genomic clone; the last numbers or characters correspond to different genomic clones from a given library. The following fragment sizes are approximate.

The genomic clones we obtained and assayed are described in Table 1 of U.S. Pat. No. 5,495,070. When the fragments were initially cloned, a SalI site was added to the fragment by the cloning vector. The designation "SalI (MboI)" in the following table is to emphasize that a naturally occurring MboI site exists adjacent to the artificial SalI site. (The genomic fragments were originally created by a partial MboI digest.) All other restriction sites in Table 1 and in FIG. 1 of U.S. Pat. No. 5,495,070 are naturally occurring genomic sites.

6. Characterization of Promoter Activity (In General)

Once the DNA was purified from the phage genomic clones (Ausubel, et al., pp. 1.10.1 to 1.13.6) the insert DNAs (10 to 15 Kb) were characterized in terms of their restriction maps (supra, pp. 3.1.1 to 3.3.2). The different restriction fragments were separated on agarose gels and Southern blotted. The blots were then be hybridized to cDNA probes. This procedure enabled us to identify smaller fragments (about 1 to 10 Kb) that contained the homologous cDNA sequence. The fragment was then subcloned (supra, pp. 3.16.1 to 3.16.11) into plasmid vectors such as pGEM5zf (Promega, Madison) or Bluescript SK, KS (Stratagene, Calif.). All further manipulations, such as promoter identifications, transcription maps and gene size determinations were done using the subclones.

Mapping the gene transcripts by nuclease protection may also be done. Single-stranded DNA probes may be generated from the Bluescript subclones and hybridized to poly(A)+ RNA from fiber cells. The hybridized portions that are protected from nuclease action will be determined as described by Calzone, et al. in Methods in Enzymology, Vol. 152 (Eds. Berger, S. L. and Kimmel, A. R.), 1987, pp. 611–632. Furthermore, mapping the 5' termini by cDNA primer extension is also described (supra, pp. 629–632). These strategies will determine the size of the gene, as well as precise boundaries of the gene transcript, or coding region for the fiber gene, in the subclone. Portions of the DNA may then be sequenced if desired.

It was then necessary to determine whether the isolated DNA fragments had promoter activity.

A GUS fusion construct was used to identify the cotton promoters. First, the transcription start site of the mRNA was determined by primer extension method, as described by Calzone, et al. (supra). The subcloned gene fragment and a short restriction fragment or an oligomer at the 5' end was used in the primer extension. A beta-glucuronidase (GUS) coding sequence along with necessary termination signals, as well a 5' leader sequences, was used with an upstream 2–3 Kb DNA fragment from the transcription or translation start site. The GUS sequence is already readily publicly available (ATCC 67641).

Figure 2:
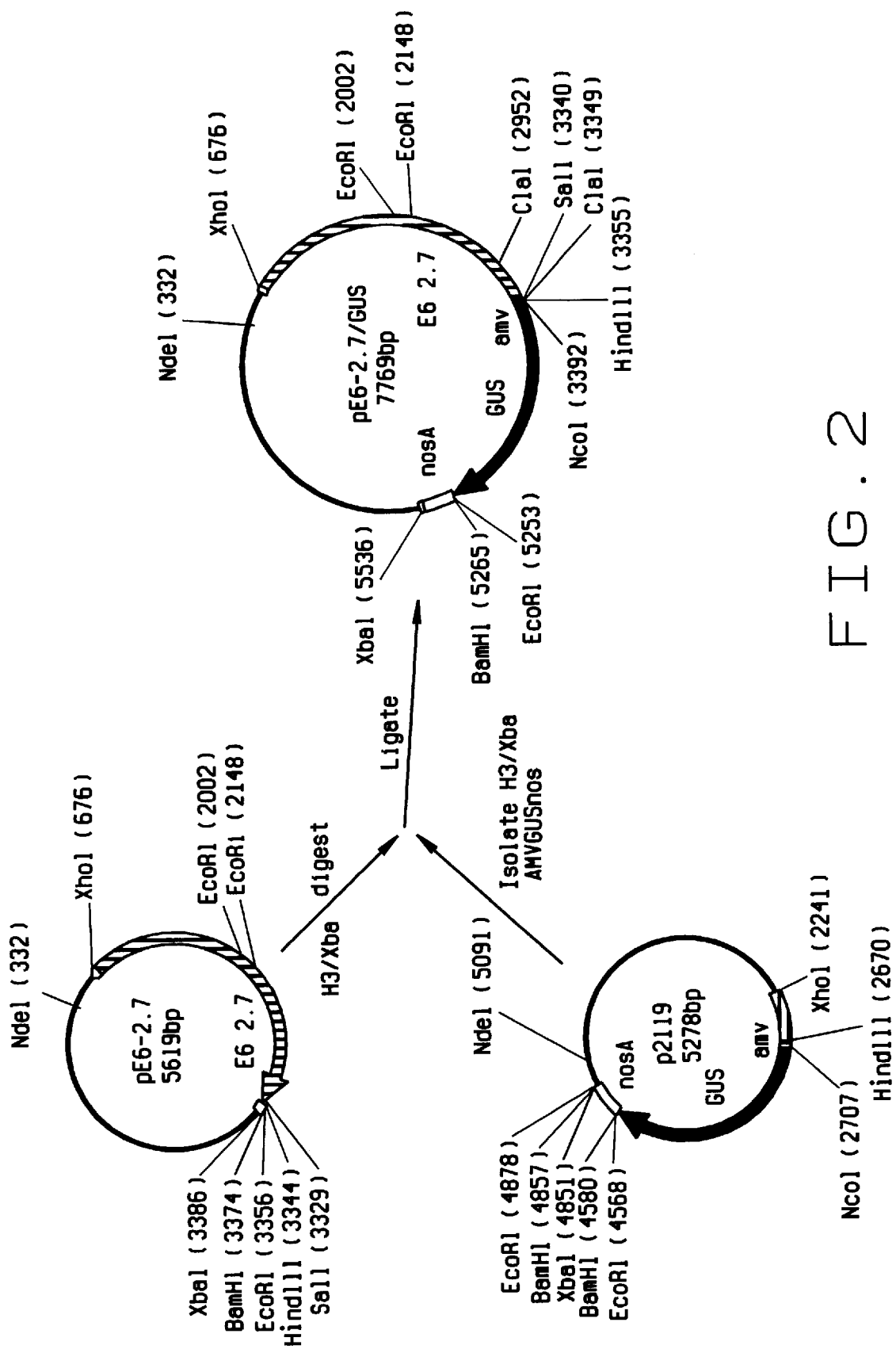
FIG. 2 is a diagram of pE6-2.7/GUS construction.

It has been demonstrated that a GUS gene construct with a cauliflower mosaic virus 35 promoter (CaMV35s) promoter is functional in plant cells. Thus, when this construct was introduced through particle bombardment (described by McCabe, D., et al., Bio/Technology, 6:923–926, 1988) into a plant, GUS activity was observed. If the construct containing an unknown DNA is found to be active in expressing GUS, then it can be concluded that the DNA fragment contains a promoter that directs the expression of GUS gene. Using the GUS assay, we determined that the sequences identified in Table 1 had promoter activity. FIG. 2 describes the various levels of promoter activity we found.

Using the Bluescript subclone and exonuclease/mung bean deletion procedure in which a series of clones with differing lengths of the 5' fragment are generated, one can identify minimum lengths of 5' DNA necessary to express the gene in fiber cells. These types of procedures will enable one to identify promoters from all genomic clones. Based on this knowledge, one can construct various developmentally regulated expression vectors containing fiber genes of interest and introduce them into plants.

7. Determination of Promoter Activity

A chimeric gene construct was made using the putative promoter and the reporter gene beta-glucuronidase (GUS) of E. coli. GUS catalyzes the cleavage of 5-bromo-4-chloro-3-indoyl glucuronide (X-Gluc). The indole derivative produced by this cleavage undergoes oxidative dimerization to form a blue dye. Cells that produce this blue dye can be detected easily. The GUS marker system has been described in detail by Jefferson, et al., in Proc. Natl. Acad. Sci. USA 83:8447–8451 (1986) and in Plant Mol. Biol. Rep. 5:387–405 (1987). The GUS gene is publicly available (ATCC Accession No. 67641).

Chimeric plasmids were constructed by litigating a promoter-less GUS coding region along with a transcription termination signal Nos(A) at the 3' end into a vector cassette as a NcoI/SalI fragment. An AMV 5' untranslated leader is added to the 5'-end of the GUS gene as a NcoI/XhoI fragment. This construct contains unique XhoI and NcoI sites for introducing putative promoters. For example, if a cauliflower mosaic virus 35s (CaMV 35s) promoter is ligated into XhoI or NcoI site and the resulting plasmid (p2119) is introduced into plant cells by particle acceleration, GUS expression can be detected. Ellis, et al., Plant. Mol. Biol. 17:19–27, 1991. We have tested GUS expression by histochemical staining as well as quantitative measurements (Jefferson, R. A., supra).

The assay involves transforming a test cotton tissue, such as hypocotyl, with different plasmids. We transformed the hypocotyl tissue via a particle-mediated transformation method disclosed in U.S. Pat. No. 5,015,580, hereby incorporated by reference.

We analyzed our reporter gene constructs in two ways, through histochemical staining and through fluorogenic analysis. The histochemical staining gave a quick "yes or no" answer while the fluorogenic analysis provided quantitative data.

(a) Histochemical Staining

Histochemical localization of beta-glucuronidase activity in plant tissues is achieved by incubating freshly cut, transformed tissue sections in a solution containing 5-bromo-4-chloro-3-indoyl glucuronide (X-Gluc). X-Gluc is prepared by dissolving 5 mg of X-Gluc in 50 $\mu$l of dimethyl formamide and diluting it to 10 ml with 50 mM sodium phosphate buffer pH 7.0. After staining (1–3 hours at 37° C.), the tissue sections were rinsed off with 70% ethanol. Cells containing an active GUS gene turn blue.

(b) Fluorogenic Assay

The quantitative assay for GUS activity depends on the cleavage of 4-methyl umbelliferyl glucuronide (MUG) by the GUS enzyme into a fluorogenic product 4-methyl umbelliferone (MU). MU is fluorescent when its hydroxyl group is ionized. (Jefferson, R. A. supra). The fluorogenic assay is carried out as follows. Plant tissue was homogenized in extraction buffer (50 mM $NaH_2PO_4$, pH 7.0, 10 mM EDTA 0.1% Triton X-100, 0.1% sodium lauroyl sarcosine, 10 mM β-mercaptoethanol). We included proteinase inhibitor PMSF at a final concentration of 20 $\mu$g/ml and 1% insoluble PVP. The extract, after centrifugation (300 $\mu$l) was added to 1 ml of MUG buffer. The MUG buffer is made up of 1 mM MUG in the above extraction buffer. The mixture is incubated at 37° C. and at time points 0, 20, 40, and 60 minutes an aliquote (100 $\mu$l) is withdrawn and added to 1 ml stop solution (0.2 M $Na_2CO_3$). The fluorescence at each time point is measured in a fluoro-calorimeter (excitation at 365 nm, emission at 455 nm) Protein concentration of the plant extract is determined by Bradford assay using a test kit from Bio-Rad Laboratories (M. Bradford, Anal. Biochem. 72:248–254, 1976). The fluorimeter is calibrated with freshly prepared MU standards. The results are given as pmole MU/mg/min. FIG. 2 of U.S. Pat. No. 5,495,070 describes the various results with twelve promoter fragments.

The above system for the detection of promoters, namely transient expression of chimeric GUS plasmids introduced into hypocotyl tissues through particle bombardment, appears to be limited in that no tissue specificity of expression is observed for any of the promoters tested. Thus, promoters (LAT 52, Cab) that were proven to be tissue specific in heterologous stable transgenic plants (Twell, et al., *Mol. Gen. Genet.* 217:240–245 (1989); Ha and An, *Proc. Natl. Acad. Sci. USA* 85:8017–8021 (1988)) are found to express GUS transiently when introduced into cotton hypocotyls by particle bombardment.

The following control experiments were conducted along with each of the promoter assays.

Figure 3:
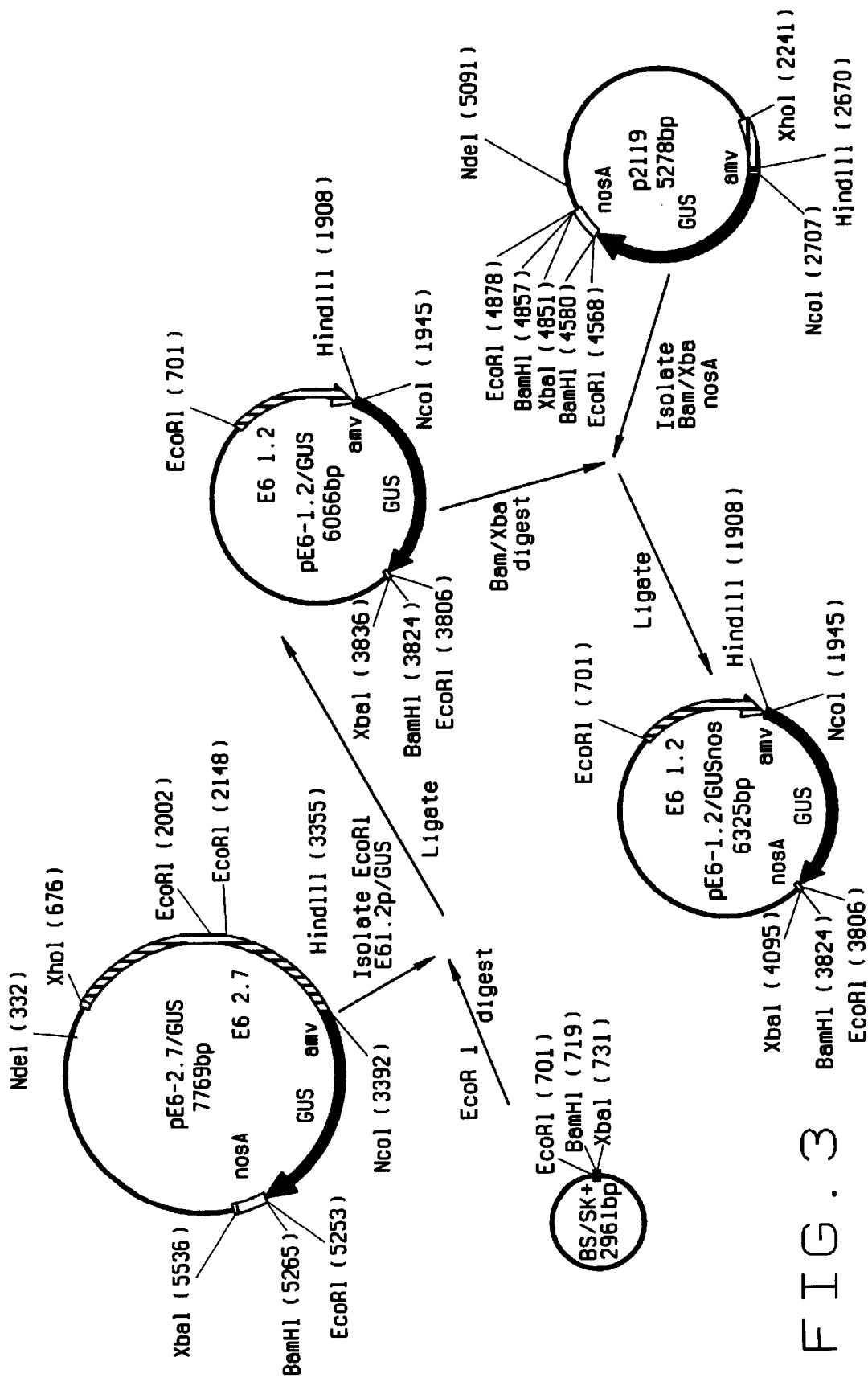
FIG. 3 is a diagram of pE6-1.2/GUS construction.

1. Plasmid p2117 was introduced into cotton or soybean hypocotyl tissues as a negative control. Because p2117 contains a promoter-less GUS gene, no GUS activity should be detected. FIG. 3 of U.S. Pat. No. 5,495,070 describes p2117.
2. The tissue was bombarded with p2119. p2119 contains a GUS gene driven by 35s promoter. This is a positive control, for GUS should always be expressed.
3. The DNA fragment being tested for activity is introduced into hypocotyl tissue. This is to demonstrate that the fragment in question has no GUS-like activity.

Using the above procedures and protocols, we have demonstrated promoter activity with twelve promoter fragments listed in FIG. 1 of U.S. Pat. No. 5,495,070. The promoters exhibited different levels of expression, as FIG. 2 of U.S. Pat. No. 5,495,070 indicates. If one wished to create a transgenic plant with high or low expression of a certain transgene, FIG. 2 of U.S. Pat. No. 5,495,070 would allow one to select the appropriate promoter.

8. Transformation of Plants

The most common methodology used for the transformation of cells of dicot plant species involves the use of the plant pathogen *Agrobacterium tumefaciens*. *A. tumefaciens* harbors a plasmid, referred to as the tumor-inducing or Ti plasmid, which has the natural ability to transfer a segment of itself, referred to as the T-DNA (transfer-DNA), into the genome of infected plant cells. Wild-type *A. tumefaciens* use this ability to genetically transform infected cells of plants so that the plant cells become tumorous, and synthesize one of a series of compounds, known as opines, which can be metabolized by the infecting *A. tumefaciens*. Several investigators have found that by removing the bulk of the T-DNA from the Ti plasmid harbored by *A. tumefaciens*, and by replacing that T-DNA with a foreign gene construction, the Agrobacterium can transform infected plant cells with the foreign gene in such a fashion that the resultant cells are not tumorous, as plant cells infected with wild-type *A. tumefaciens* normally are. The foreign gene construction is then included in the cells of a whole plant regenerated from the transformed cells and is then inherited in a simple Mendelian manner. The construction can thus be treated as any inheritable trait for crop breeding purposes. The transformation and regeneration of cotton plants by Agrobacterium transformation has been achieved and reported. Umbeck, et al. (supra) and Firoozabady, et al. (supra).

Other methods of plant transformation, such as transformation by accelerated particle carried DNA, are now available (McCabe, et al., supra). An apparatus capable of performing particle-mediated transformation is commercially available from BioRad. In any event, once the creation and assembly of plant expression vectors including fiber specific gene sequences is accomplished, the transformation and regeneration of cotton plants with these expression vectors is within the ability of one of ordinary skill in plant genetic engineering, and is not dependent on the method of transformation.

9. Characterization of Cotton Genes

As a specific Example of our characterization of fiber-specific promoters, our characterization of the E6 genes is disclosed in detail. Brief descriptions of other genes and promoters follow.

Two E6 genes from cultivar Sea Island (*G. barbadense*) and two genes from Coker 312 (*G. hirsutum*) were isolated and examined. These four genes have homology to each other. Detailed structural characterization of these genes is presented below.

a. Sea Island E6-2A Gene and Promoter.

The phage EMBLSIE6-2 contains a 14.2 Kb insert. Restriction mapping followed by Southern analysis showed that a 9.5 Kb SalI fragment hybridized to E6 cDNA. The 9.5 Kb SalI fragment was subcloned into Sk$^+$ vector (pSkSIE6-2A). Further subcloning resulted in a shorter clone (6.4 Kb) pSKSIE6-2AH3. About 541 bp of promoter region, 33 bp of 5' noncoding region, 741 bp of coding region, and 332 bp of 3' noncoding region have been sequenced and is described in SEQ ID NO:20 of U.S. Pat. No. 5,495,070. In order to identify the promoter region, plasmid pSKSIE6-2AH3 was digested with NcoI and BamHI to liberate three fragments. The vector and upstream 5' noncoding fragment of the gene (4.5 Kb insert and 3 Kb vector) was gel purified and subjected to Elutip-d column elution.

Figure 4:
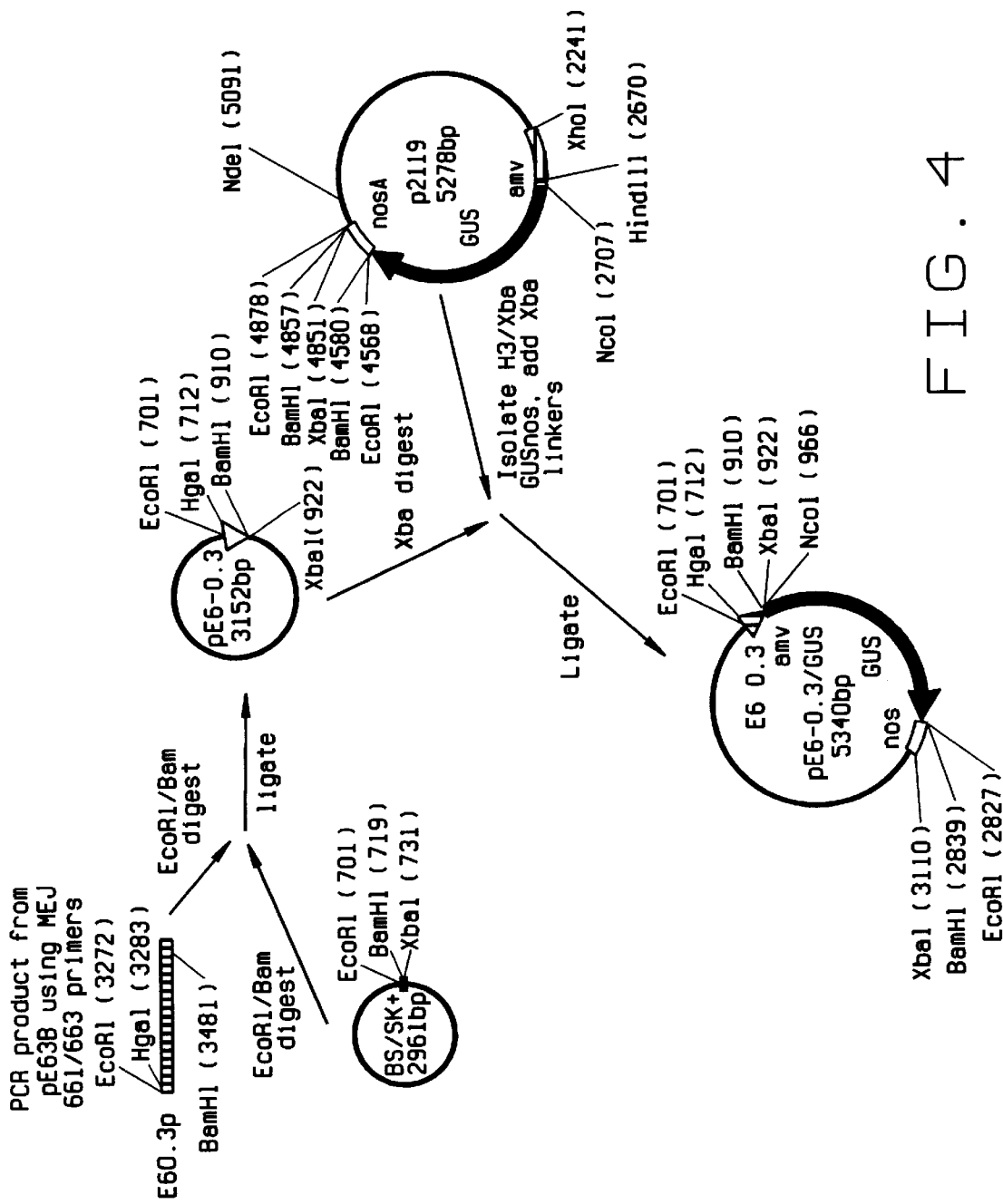
FIG. 4 is a diagram of pE6-.3/GUS construction.

Plasmid 2117 is a promoter-less GUS marker gene cassette. A circular map of the plasmid is shown in FIG. 3 of U.S. Pat. No. 5,495,070. When a 35s promoter is added to p2117, the marker gene is able to express GUS in plant tissue. Plasmid 2117 was digested with NcoI and BamHI and gel purified. The 2 Kb NcoI/BamHI fragment containing the GUS gene was ligated to the 7.5 Kb E6 genomic-vector fragment and transformed into XL-1 Blue cells. Recombinant clones (p2117-E6) were identified by SDS-agarose gels. However, this construct lacks a poly(A)-addition signal. Therefore, a 277 bp BamHI fragment of p2117, which contains the poly(A)-addition signal, was ligated into the BamHI site of p2117-E6. The orientation of the poly(A) addition signal in p2117E6P-2A was then determined by restriction digestion analysis and the chimeric plasmid containing the correct orientation was selected. The construction of the plasmid is shown in FIG. 4 of U.S. Pat. No. 5,495,070.

Plasmid p2117E6P-2A was then introduced into cotton hypocotyls through particle acceleration method (McCabe, D., et al., *Bio/Technology*, 6:923–926 (1988)). As mentioned above, control experiments used plasmids p2119, p2117, and pSKSIE6-2AH3. Plasmid p2119, a GUS construct with the 35s promoter gave positive GUS activity as expected. Plasmid 2117 (no plant promoter) and plasmid SKSIE6-2AH3 (no GUS gene) gave no GUS activity. Plasmid p2117E6P-2A which contains the region 5' to the E6 gene and the GUS gene, showed GUS activity. This result suggests that an active promoter element is located in the 4.5 Kb NcoI/SalI DNA fragment.

b. Sea Island E6-3B Gene and Promoter.

Figure 5:
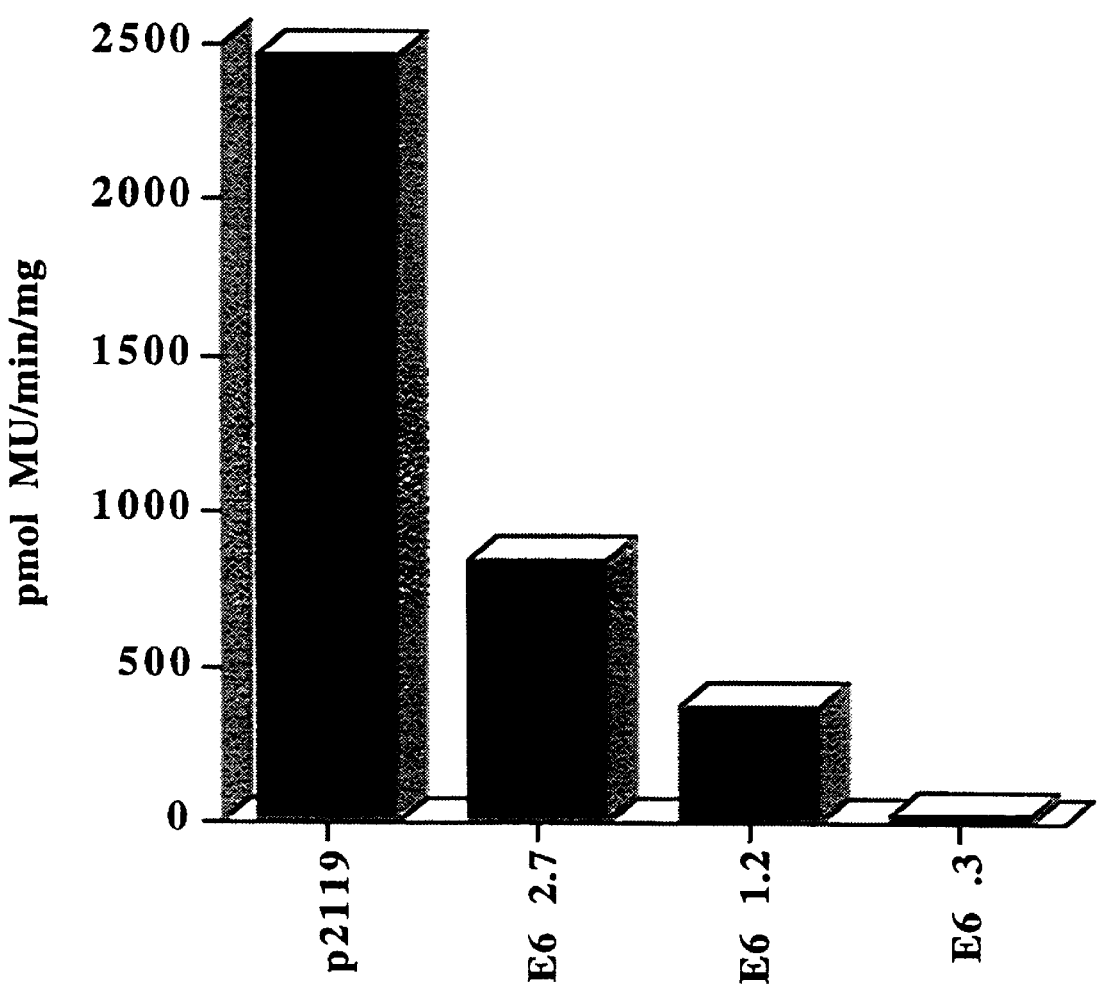
FIG. 5 is a summary of MUG assay results for the plasmids of FIGS. 2–4.

A second phage (insert 15 Kb) hybridizing to E6 cDNA contains a SalI fragment (5.1 Kb). This fragment was subcloned into SK$^+$ vector. This plasmid (pSKSIE6-3B) was characterized in terms of the region to which E6 cDNA hybridize. 581 bp of promoter region, 33 bp of 5' noncoding region, 741 bp of coding region, and 313 bp of 3' noncoding region are shown in SEQ ID NO:21 of U.S. Pat. No. 5,495,070. Promoter fragment identification of pEKSIE6-3B gene was carried out as follows. After determining the coding region and the putative promoter region in pSKSIE6-3B it was digested with NcoI and XbaI and the resulting plasmid (approximately 5.7 Kb) gel purified. Similarly the promoter-less GUS gene cassette was digested with NcoI/XbaI and gel purified. The GUS gene was then ligated to plasmid pSKSIE6-3B. Construction of p2117 E6P-3B is shown in FIG. 5 of U.S. Pat. No. 5,495,070. As described for p2117E6P-2A, various control plasmids along with p2117E6P-3B were introduced into hypocotyl to test promoter activity. p2117E6P-3B showed GUS expression indicating that the 2.7 Kb NcoI/SalI E6-3B fragment contains the promoter of E6-3B gene. Relative expression level of E6-3B promoter is shown in FIG. 2 of U.S. Pat. No. 5,495,070.

c. Coker E6 Gene pSKCKE6-1A and Promoter.

The screening of a Coker 312 genomic library with pCKFb15A1-E6 cDNA resulted in the identification of two phages, DASHCKE6-1A and DASHCKE6-4A. Inserts from these two phages were subcloned into SK+ vector.

A 12 Kb insert from phage DASHCKE6-1A was subcloned into SK+ vector to give pSKCKE6-1A plasmid. A detailed restriction map of the insert was prepared and its comparison with the map of pCKFb15A1-E6 enabled us to locate the coding region of Coker E6 gene in pSKCKE6-1A. About 567 bp of promoter, 33 bp of 5' noncoding region, 717 bp of coding region, and 301 bp of 3' noncoding region are included in the sequence and is shown in SEQ ID NO:22 of U.S. Pat. No. 5,495,070. A 4.1 Kb NcoI fragment upstream of the coding region most likely contains the promoter of this gene. To confirm this, the NcoI fragment was ligated into the NcoI site of p2117 and the construct was tested for GUS activity as described earlier. The results demonstrated that the 4.1 Kb fragment contains a promoter.

d. Coker E6 Gene PSKCKE6-4A and Promoter.

An 8.0 Kb SalI fragment from a second phage (12.2 Kb insert) hybridized to E6 cDNA. This fragment was subcloned into SK+ vector (pSKCKE6-4A). 512 bp of promoter region, 37 bp of 5' noncoding region, 726 bp of coding region, and 303 bp of 3' noncoding region have been sequenced and is shown in SEQ ID NO:23 of U.S. Pat. No. 5,495,070. In a manner similar to our work with pSKCKE6-1A, we determined the location of the promoter of this gene and subcloned a 3.9 Kb NcoI/SalI fragment into p2117 at the XhoI/NcoI sites. The resulting plasmid was then tested for GUS activity and was found to be able to direct synthesis of GUS enzyme in plant tissue.

e. Characterization of *Cebia pentandra* (Kapok E6 Gene and Promoter.

An EMBL-3 genomic library of *Cebia pentandra* (Kapok) was screened with E6 cDNA. Four hybridizing phages were identified. One of the phage inserts was subcloned into SalI site of Bluescript vector SK+. The resulting clone, pSKCPE6-3A (15.3 Kb insert) was characterized by restriction analysis and Southern blotting. We identified a SalI-EcoRV fragment (4.8 Kb) that hybridizes to CKFB15A1-E6. This fragment was subcloned into the SalI-EcoRV site of Bluescript vector resulting in clone pSKCPE6-3A-RV. A 1.6 Kb stretch of DNA was sequenced and is shown in SEQ ID NO:24 of U.S. Pat. No. 5,495,040. Comparison of cotton E6 cDNA sequence and Kapok E6 gene sequence revel 84.3% homology.

Figure 6:
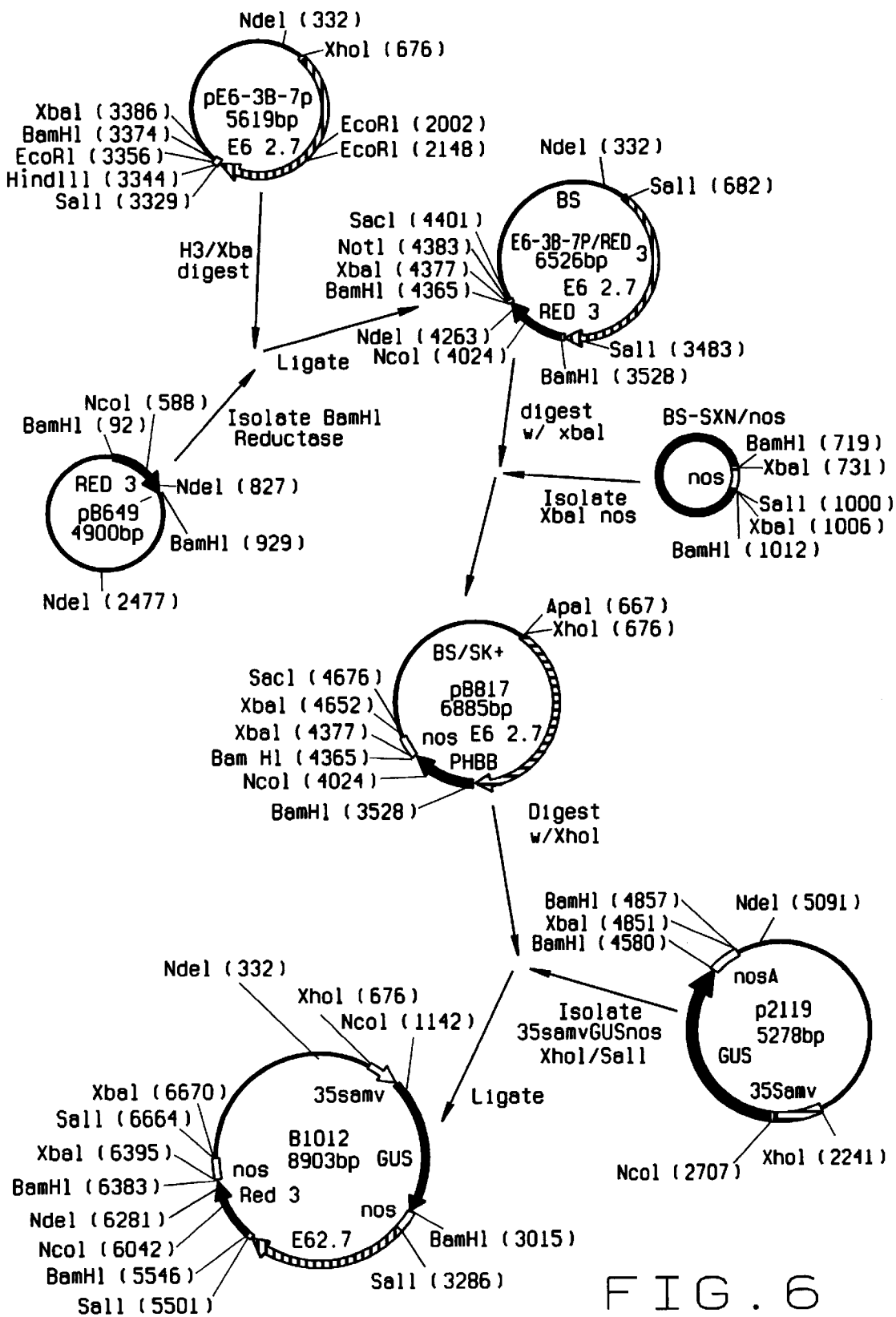
FIG. 6 diagrams the construction of the E6-3B-2.7 kb-acetoacetyl CoA reductase plasmid.

Plasmid SKCPE6-3A-RV was digested with NcoI and BamHI and the fragments separated on agarose gels. The larger of the DNA fragments (6.2 Kb, a 3.2 Kb insert and a 3 Kb vector) was electroeluted and purified. Similarly, GUS gene containing p2117 was digested with NcoI and BamHI and the 1.8 Kb GUS fragment isolated and purified. The two DNA fragments were then ligated and transformed into X1-1 Blue cells. Recombinant clones were identified by DNA analysis on SDS-agarose gels (Sekar, et al., supra). A Nos poly(A) signal region from p2117 was isolated by BamHI digestion. This fragment was ligated into the BamHI site of the above Kapok E6-GUS plasmid after linearization with BamHI. The resulting clones was analyzed for correct orientation of the Nos poly(A) addition signal by restriction digestion analysis. A circular map of pCPE6-2117 is shown in FIG. 6 of U.S. Pat. No. 5,495,040.

Plasmid CPE6-2117 was introduced into cotton hypocotyls through particle acceleration method (McCabe, et al., (supra). In duplicate experiments, pSKCPE6-RV, p2117 and p2119 were introduced into hypocotyls. As described earlier, GUS activity was assayed. As expected, pSKCPE6-RV and p2117 showed no GUS activity while p2119 gave positive results. The plasmid CPE6-2117 showed GUS activity, confirming that the 3.2 Kb SalI/NcoI fragment contains the promoter for CPE6 gene.

f. Characterization of B8 Gene and its Promoters

The insert of B8 cDNA clone was used to isolate a phage from Sea Island genomic library (19 Kb insert). A SalI/BamHI fragment from the phage DNA that hybridized B8 cDNA insert was subcloned into SK+vector. This generated a 9.5 Kb fragment that contained the B8 gene. A 2.5 Kb DNA part was then sequenced and was shown to contain homologous sequences to B8. SEQ ID NO:28 of U.S. Pat. No. 5,495,070 is the B8 gene. Based on the sequence comparison of the cDNA and gene, we determined that a 2.1 Kb BamHI/BstBI fragment would contain the B8 promoter. In order to create an NcoI site at the 3' end of the promoter fragment for convenient cloning of genes, we modified the B8 promoter by PCR. Two PCR primers MEJ117 and MEJ1118, (SEQ ID NO:30 and SEQ ID NO:31 of U.S. Pat. No. 5,495,070) were used to amplify a 120 bp fragment. MEJ118 contained a BstBI and an NcoI site. The PCR product was digested with BstBI and purified. Similarly the B8 vector, pSKSIB8 clone was also digested with BstBI and a 7.Kb fragment was gel purified and ligated to the PCR product. Recombinant clones containing the B8 vector were then screened and the orientation of the 120 bp insert in B8 was determined by PCR. Now the plasmid was ready for determination of B8 promoter activity. The plasmid described above was digested with NcoI and SalI and gel purified. A GUS-containing clone pSIB8GUS was then introduced into cotton hypocotyl tissue through particle bombardment. Appropriate control experiments were included. These studies show that B8 fragment contains promoter activity.

10. Characterization of FbLate genomic clones

The DNA insert in pSKSIFbLate2-82A was characterized by restriction analysis and Southern blot hybridization. This process resulted in the identification of a 1.5 kb ScaI fragment that hybridized strongly to the FbLate-2 cDNA. In addition there were two other fragments, a 4 kb NcoI fragment and 800 bp ScaI fragment that showed weak hybridization. Based on the cDNA sequence, the 4 kb NcoI fragment is likely to contain the 5'-end of the gene along with the promoter. FIG. 1 of U.S. Ser. No. 08/298,829 shows the restriction map of pSKSIFbLate2-82A. Based on the hybridization pattern, it appeared that the FbLate-2 gene is localized within a 6.3 kb region flanked by NcoI and ScaI sites. In order to locate the gene more precisely, we used primers based on the FbLate-2 cDNA to sequence the gene.

The nucleotide sequence of a 3974 bp region of pSKSIFbLate2-82A clone was determined and is shown in SEQ ID NO:3 of U.S. Ser. No. 08/298,829. (We shall refer to the clone described above as the FbLate2-82A gene.) Comparison of the FbLate2-82A gene sequence with that of FbLate-1 and FbLate-2 cDNA sequences showed that both cDNAs were homologous to the gene. In case of FbLate-1 cDNA, the sequence similarity was 92.4% while that of FbLate-2 was 98.9%. A comparison of the nucleotide sequence of the FbLate2-82A gene with those available in the GenBank data bank showed that the gene is not homologous to any other sequences. The comparison was carried out using GCG program FASTA in April 1996. Small regions of similarities were found with a number of genes. Examples are 52.4% similarity in a 430 bp region of the *C. elegans* mitochondrial genome and a 59.6% similarity to a 350 bp region of *P. falciparum rhoptry* associated protein 1.

The FbLate2-82A gene sequence had a long open reading frame spanning 1061 bases. An ATG initiation codon was present at position 2315. In order to determine the location of the start codon of the FbLate2-82A gene, we undertook cloning of the remaining piece of the FbLate-2 cDNA by a modified polymerase chain reaction, the rapid amplification of cDNAs (RACE; Saiki, et al., *Science* 239:487–491, 1988; Frohman, et al., *Proc. Natl. Acad. Sci. USA* 85:8998–9002, 1988).

As described below, the FbLate-2 cDNA is a partial clone of 645 bp. Based on the northern analysis, the FbLate-2 transcript is about 1300 bases long. Thus, it appears that about 650 bases of the 5'-end of this clone was missing. In order to clone the missing 5'-end we used "RACE," which is a PCR protocol that generates cDNAs by amplifying copies of the region between a single point in the transcript and the 5'-end. Two primers based on the sequence of cDNA clone A11 were synthesized (SEQ ID NOs:11 and 12) and used to PCR-amplify the 5'-end of the FbLate-2 mRNA. We used a RACE kit from Clontech Lab. (Palo Alto, Calif.). The kit contained an AmpliFinder anchor and AmpliFinder anchor primer that are necessary to complete the reaction. Detailed protocol of RACE is described in *PCR protocols, A guide to methods and applications*, Eds. Innis, M. A.; Gelfand, D. H.; Sninski, J. J.; and White, T. J., Academic Press, NY, pp. 28–38, 1990, as well as instructions from the kit supplier.

The insert from one of the clones (519 bp) was then sequenced (SEQ ID NO:16 of U.S. Ser. No. 08/298,829) and compared to the sequence the genomic clone, FbLate2-82A. The clone showed a 91.6% similarity at the nucleotide level. The homology of the RACE product started from nucleotide position 2269 of the FbLate2-82A gene. At position 2315 of the gene there was an ATG initiation codon.

A second RACE product was also generated using primers based on the sequence of cDNA clone A8. We used two primers (SEQ ID NOs:13 and 14 of U.S. Ser. No. 08/298, 829) and generated an insert of 420 bp (SEQ ID NO:15 of U.S. Ser. No. 08/298,829). The sequence of the second race clone also was determined and compared to that of the FbLate2-82A gene. The nucleotide comparison showed 91.7% similarity. Moreover, the homology started at position 2269. These findings implicate that the FbLate-2 mRNA is transcribed from the region of the 2269 nucleotide. The ATG at position 2315 is likely to be the initiation codon.

When the nucleotide sequence was translated into protein starting with the ATG at 2315, a 354 amino acid protein sequence was derived. The protein had a calculated molecular mass of 43.4 kDa with an isoelectric point of 5.97. Predominant amino acid residues of the protein were glutamic acid (26.3 mole %) and lysine (18.9 mole %). Assessment of the hydrophilicity showed the protein to be hydrophilic. There was a small hydrophobic region at the N-terminus, but otherwise the protein is hydrophilic in nature.

A computer search of the nucleotide derived amino acid sequence of FbLate2-82A gene with the available protein sequences in the data bank revealed no significant homology with any of the proteins as of April 1996. Based on these analyses we conclude that the gene we described here has not been identified from other organisms. The function of the gene is not known.

11. Determination of Promoter Activity of FbLate Promoter

A chimeric gene construct was made using the putative promoter and the reporter gene beta-glucuronidase (GUS) of *E. coli* as described above for other fiber specific promoters.

Chimeric plasmids were constructed by ligating a promoter-less GUS coding region along with a transcription termination signal Nos(A) at the 3'-end into a vector cassette as a NcoI/SalI fragment. An AMV 5' untranslated leader is added to the 5'-end of the GUS gene as a NcoI/XhoI fragment. This construct (p2117, FIG. 2 of U.S. Ser. No. 08/248,829) contains unique XhoI and NcoI sites for introducing putative promoters.

12. Transformation a. In General

We chose to use accelerated particles to transform cotton with the DNA constructs. A style of apparatus for accelerating such particles has been described in detail in U.S. Pat. No. 5,015,580 (hereby incorporated by reference). In brief, small metal particles are coated with nucleic acid material and accelerated into target cells. By an unknown mechanism, a certain percentage of the target cells will incorporate the nucleic acid.

Other particle acceleration apparatus, such as the commercially available BioRad (Biolistics) PDS-2000 particle acceleration instrument, will be suitable for the present invention. Other non-accelerated particle methods are also suitable. Such methods include electroporation, viral vectors, and Agrobacterium-mediated transformation.

Stable integration and expression of foreign genes in cotton plants has been demonstrated and repeated. Umbeck, et al., *Bio/Technology* 5[3]:263–266 (1987); Firoozabady, et al., *Plant Mol. Biol.* 10:105–116 (1987). In each of these references, the transformation of cotton tissues is accomplished by Agrobacterium infection and regeneration. Although a lengthy process, the Agrobacterium-mediated transformation of cotton has also been practiced by other laboratories and can now readily be replicated by those of ordinary skill in plant genetic engineering.

It is to be understood, however, that new methods for the transformation of cotton plants and lines are being studied, and that the transgenic cotton plants and lines with the promoters of the present invention will prove advantageous and useful regardless of the method of transformation of the original tissues. The description below suggests a preferable method of transformation.

b. Surface Sterilization

We have developed a cotton transformation system that is particularly advantageous for the practice of the present invention. The process begins with commercial cotton seed, which must be sterilized. In our example, we used DP-50 cotton seeds, although other varieties would be equally suitable. We chose DP-50 because it is a cotton variety with good growing characteristics but a coarse fiber.

A sieve beaker system is autoclaved. A sieve beaker system is a beaker with dozens of holes drilled in its bottom that can be nested inside a non-drilled glass beaker. It is also useful to utilize a third sterile beaker for rinsing the seeds so that the sieve beaker can be rested in the sterile beaker while discarding wash water.

The sieve beaker is filled with cotton seeds. The beaker into which the sieve beaker is nested is then filled with a mixture of 50% Chlorox bleach so as to cover the seeds. The seeds are allowed to rest within the bleach solution for three minutes. The bleach is drained and the seeds are then rinsed five times with distilled water.

The surface sterilized cotton seeds are then placed in a sterile glass beaker. A cotton antibiotic sterilization medium is added to the beaker at twice as much volume as there are seeds. This medium consists of sterile distilled water to which has been added carbenicillin at 200 mg per liter, cefotaxime at 125 mg per liter, and 30 mg each of BRAVO WP, BENLATE 50 DF, and CAPTAN 50 WP per liter. The seeds are incubated in the sterilization medium for three to four hours in the dark at room temperature.

Then the seeds are drained by pipette. The beaker is refilled with fresh cotton antibiotic sterilization medium and the seeds are incubated for an additional three hours.

The seeds were then drained and incubated overnight at 15° C. in the dark to germinate. If germination proceeds appropriately, the seed germination could be stopped by refrigeration at 4° C., for up to three days following the germination process.

c. Seed Dissection

After the germination of the seeds, or the removal of the germinated seeds from storage, seeds are selected that are just beginning to germinate. Overly germinated or ungerminated seeds are discarded. The proper stage of germination is defined as fully imbibed seeds with one to four millimeters of the radicle exposed. Under sterile conditions, the seed axis is removed out of the seed. This is done by manual manipulation with gloved hands to remove the seed axis from both of its cotyledons and its seed coat. The process is relatively easy to perform with practice. It is possible to readily develop the ability to pop the seed coat axis apart from the seed, without damaging the seed axis, or leaving any of the cotyledon on the seed axis.

The excised seed axis is then washed in three to four rinses of sterile distilled water. The washed but undissected explants are either dissected immediately or stored by plating on standard OR ccb medium made with fresh benzylaminopurine or BAP, but no NAA. This media is described by Barwhale, et al., *Planta*, 167:473–481 (1986), but without the NAA hormone. The explants are plated on the agar surface by being laid on their side. The excised embryonic seed axis plated on the agar medium are incubated at 15° C. in the dark overnight.

d. Exposing The Meristem

The washed seed axis explants are now ready for micro dissection to expose the meristems of the seed axes. This dissection is performed under sterile distilled water and with sterile tools. The dissection consists of removing the embryonic leaf, or leaves if there is more than one, that obscure the meristem on each of the excised seed axes. The fully dissected explants are transferred to another petri dish containing sterile distilled water.

e. Pre-Blast Hormone Treatment

After all the dissections are completed, the explants are again washed in three to five rinses of sterile distilled water. The free water is removed by pipette after the final rinse. The treated explants are then laid on their side on the surface of standard OR ccb medium made with fresh BAP but not NAA. The explants are incubated overnight, or for 24 hours maximum, at 15° C. in the dark. The treated excised embryonic axes with exposed meristems are now ready for the accelerated particle transformation blast.

f. Genetic Material And Carrier Particle Preparation

Ten milligrams of amorphous crystalline gold powder, or of an equal mixture of 1–3 micron gold spheres and crystalline gold powder is measured into the bottom of a 1.5 ml Eppendorf microfuge tube. Care is taken to ensure that the gold did not spill on the sides of the tube, since that would make it difficult to resuspend the gold due to the small volumes used in the preparation process. 100 µl of 0.1 M spermidine (free base) is added to this microfuge tube and the microfuge tube is vortexed well. 1 to 20.0 µg of double-stranded DNA is then added to the microfuge tube and the tube is then vortexed gently but completely. While the DNA/carrier particle mixture is gently vortexed, 100 µl of 2.5 M $CaCl_2$ is added to the tube. The vortex is stopped, and precipitation is permitted for 10 minutes at room temperature. The preparation could be stored at this point for some time. Shortly before use, the mixture of DNA and carrier particles is given a brief spin in a microfuge. The cleared supernatant is removed completely, and the precipitant consisting of the DNA and carrier particles is resuspended in 20 ml of 100% ethanol. The resuspended DNA and carrier particle mixture is then sonicated in a water bath sonicator for two to three brief one second exposures. The resulting suspension is then coated onto the carrier sheet, at a calculated rate of 0.05 milligrams per square centimeter of the carrier sheet. After allowing the gold to settle, the excess ethanol is drained away and the sheet is dried. These preparations of DNA and carrier beads are made fresh daily.

g. Blasting

At this point in the process, the carrier sheets are placed upon the apparatus for the blasting process. This procedure and apparatus are similar to that disclosed in U.S. Pat. No. 5,015,580, which is hereby incorporated by reference. The cotton explants are plated on 12% xanthin gum target plates. Using the normal germination and pre-blast hormone treatments described above, typically 25 explants are found to fit on each of the target surface within the blast area.

The parameters used for the particle-mediated transformation blast itself includes a relatively high electric discharge voltage through the gun, typically in the range of 15–25 kilovolts. The standard voltage used is 18 KV. The voltage is adjusted to achieve a level of impact on the treated axes such that the rate of survival of the meristems is between 40% and 90%. In other words, the blast force is adjusted to a level such that at least some of the meristems are rendered non-viable by the process. The blasting experiments are conducted at 350 ml of mercury, with helium introduced at a rate of 1.5 L per minute at atmospheric levels, and approximately 5.0 L per minute under the vacuum.

Each of the target tissues is blasted once or twice during the same day. Target tissues blasted twice in the same day are blasted once in the morning and once in the afternoon, with the explants stored between successive blasting procedures in a moist chamber at approximately 28° C. in the dark. The target tissues are placed in the dark immediately after each blasting exposure.

h. Post-Blast Protocol

The explants are now removed from the target surface, and plated in a normal orientation on OR ccb medium made with fresh BAP but no NAA. Care is taken not to expose the explants to excessive light. Care is taken to keep the meristem from contact with any media, and no wet plates are utilized. The fresh explants are plated and then incubated at 28° C. in the dark for one to two full days.

One day after the blasting, a preliminary assessment of transient enzyme activity is conducted on the resultant tissues. The assay is conducted at this time to check for the quality of the bead preparation protocol, and also to look specifically at the number of transformation events in the meristem, a rough approximation of which can be made by checking the transient activity of the explants at this stage. Although due to the heavy damage from the blasting process 20% to 60% of the meristems are sufficiently damaged so as to never produce shoot, those same damaged meristems will, upon assay, exhibit excellent transient gene activity particularly of the GUS gene using this procedure. Thus, the tissues can be assayed at this step for the percentage of GUS activity, even though shoots are not yet evident on the meristems subjected to the procedure.

Following the initial post-blast incubation on the medium described above, the cotton explants are transferred to the dextrose-based woody plant medium (WPM), minus BAP plus carbenicillin and benoxyl, in plantcons again under low light. The WPM medium mixture, based on Lloyd and McCown, *Proc. International Plant Propagation Soc.* 30:421–427 (1981) is prepared as follows: $NH_4NO_3$ (400 mg/L), $Ca(NO_3)_2.4HOH$ (556 mg/L), $K_2SO_4$ (990 mg/L), $CaCl_2.2HOH$ (96 mg/L), $KH_2PO_4$ (170 mg/L), $H_3BO_3$ (6.2 mg/L), $Na_2MoO_4.2HOH$ (0.25 mg/L), $ZnSO_4.7HOH$ (8.6 mg/L), $CuSO_4.5HOH$ (0.025 mg/L), $FeSO_4.7HOH$ (27.8 mg/L), $Na_2EDTA$ (37.3 mg/L), Thiamine.HCL (1.0 mg/L), Nicotinic acid (0.5 mg/L), Pyridoxine.HCl (0.5 mg/L), Glycine (2.0 mg/L), Myo-inositol (100 mg/L), Dextrose (20 g/L), Agar (3.0 g/L), Gelrite (1.1 g/L), Calcium gluconate (1.29 g/L), Carbenicillin (200 mg/L) and Benoxyl (60 mg/L). The tissues are incubated at 28° C. in the dark for one to seven days.

Following the culturing steps outlined above, the plantcons are then moved to full light exposure so as to induce shoot development in the tissues under cultivation.

i. Identification of Transformant Events

The plantcons are then moved to a cultivation chamber and exposed to 16 hour light periods at 28° C. A number of cultured explants then proceed to exhibit shoot elongation and development from the plated tissues. It then becomes necessary to evaluate the growing shoots to ascertain the level of germ line transformation events which are achieved through this process. The assay procedure is conducted at such a point that the shoots each have developed their first leaves. The outermost one-third to one-half of each leaf is then cut off completely across the leaf through the midrib. The leaves are then assayed for GUS activity to identify GUS-positive expressing plants.

At this point, the quality of the event is characterized depending on the level of GUS activity in the leaf. Some of the leaves exhibited only uneven or irregular GUS expression, indicating chimeric plants. Based on the results below and experience with other plant systems, we have observed and verified that a transformation of the vascular system, as exemplified by the leaf petiole, correlates very well with the occurrence of a germline transformation event. Some of the leaves seemed to be totally blue, indicating putatively clonal transgenic plants. If the plant is characterized as germline transformed, the plant is transferred into rooting conditions and grown out in the greenhouse. For chimeric plants, the plant is pruned to just above the transformed leaf so as to force the axillary bud to grow from the transformed area of the plant after which it is retested.

For plants that tested negative, the leaves are removed, and the plants are cultured until newly formed leaves are regenerated. Tests are again conducted. This process is repeated three times before a final negative determination for the plants is made.

The entire process as described above, from initial plating of the seeds to the recovery of an initial generation transgenic plant requires approximately three to five weeks. Based on the initial results as described above, we expect that approximately one mericlonal transgenic plant will occur per approximately 100 to 500 meristems exposed to the blasting process. Of the mericlonal plants produced from the process, approximately 0.1%–1.0% will be found to have transformed germ lines. Thus, although the yield may seem low, this process allows for the relatively rapid and more inexpensive generation of large numbers of transgenic plants than other procedures because the process can be performed quickly. The transgenic plants will transmit the inserted genes by Mendelian inheritance, and the process can be performed directly on elite cotton lines, even Sea Island and Pima lines, which are resistant to tissue-culture methods.

13. Cloning of Acetoacetyl CoA reductase and PHB synthase Acetoacetyl CoA Reductase The DNA sequence of acetoacetyl CoA reductase gene was reported in Peoples and Sinskey, *J. Biol. Chem.* 264:15293–15297, 1989 and in U.S. application Ser. No. 08/241,943, filed May 12, 1994, inventor M. John (both hereby incorporated by reference). The reductase gene was cloned by PCR amplification from *A. eutrophus* using MEJ76 and MEJ77. MEJ76 contains a BamHI site and MEJ77 contains a XbaI site. This amplification created a 741 bp fragment that was cloned into BamHI/XbaI sites of SK+ vector. This resulting plasmid is referred to as PHB-B. The coding sequence of the Acetoacetyl CoA Reductase gene can be taken from Peoples and Sinskey (supra).

The PCR product of acetoacetyl CoA reductase was sequenced and compared with the published sequence. Four nucleotide changes were observed. Starting from the initiation codon, nucleotide "A" at position 433 was changed to nucleotide G. This would result in an amino acid change from lysine to arginine. A second change was detected at position 497 where a C was changed to a T in the PCR product. This will cause an amino acid sequence change from alanine to valine in the PCR product. Further, at position 556 nucleotide "A" was changed to a G. At position 557, a T was changed to C. These two changes result in a change of amino acid from isoleucine to alanine.

In order to test whether the PCR-produced acetoacetyl CoA reductase gene could be translated into a product with the correct molecular size, we conducted the transcription/translation-coupled reticulocyte lysate experiment. A protein of 27 kDa was obtained. The size of this product agrees with the know molecular weight of this enzyme.

The enzymatic activity of the acetoacetyl reductase gene was tested in the transcription/translation coupled in vitro system (supra). No activity was detected. The gene was excised by digestion with BamHI/XbaI and treated with Klenow polymerase to blunt the ends. BamHI linkers were then added. The gene was then cloned into expression vector, DR 540 as a BamHI fragment and orientation determined by restriction map analysis. Cells containing either sense or antisense plasmids exhibited no reductase activity after IPTG induction. Thus, it is apparent that the substitutions in the gene may have caused the loss of enzymatic activity of the protein. Therefore, we repeated the PCR cloning of reductase under PCR conditions to increase the fidelity of the system (Innis and Gelfand in *PCR Protocols*, Eds. M. A. Innis, D. H. Gelfand, J. J. Sninsky, T. J. White; pp. 1–12, 1990). Primers MEJ76 and MEJ305 and a second set of primers, MEJ76 and MEJ304 were used along with 50 micromolar dNTPs, 0.5 unit of Taq polymerase and 5 μl of bacterial culture. Other conditions were similar to those described earlier (supra). MEJ304 and MEJ305 contain BamHI sites. MEJ305 primes at the stop codon of the reductase gene while MEJ304 primes 99 bases downstream of the stop codon. Hence, the PC product of MEJ76/305 will have only the coding region of reductase and is referred to as PHB-Bs, while the PCR product of MEJ76/304 will result in coding region and 99 bases of 3' untranslated region. The longer insert is referred to as PHB-B1.

The PCR products after BamHI digestion were cloned into BamHI sites of SK+ vector. After determination of orientations we conducted transcription/translation reactions with the genes in the SK+ vector. Both PHB-Bs and PHB-B1 were found to express active enzyme. We also cloned the PHB-B1 and PHB-Bs inserts into DR540. Cells containing sense orientation of the genes exhibited reductase activity while those with antisense genes showed no activity.

From these experiments we conclude that substitutions at nucleotide positions 433, 497, 556, 557 are detrimental to the activity of the reductase gene.

14. Identification of Essential Fiber-Specific Promoter Regions

As described above, we have isolated several cotton promoters and demonstrated that these promoters are capable of directing transgene expression in transgenic cotton (see also U.S. Pat. No. 5,495,070; John and Crow, *Proc. Natl. Acad. Sci.* 89:5769–5773, 1992; John, *Plant. Mol. Biol.* 30:297–306, 1996). Now we are studying the cotton promoters to understand the DNA regions responsible for tissue and developmental regulation in cotton. A series of deletions were made from representative promoters and linked to marker genes. These chimeric constructs were introduced into cotton through particle bombardment and gene expression assayed. From these results we conclude the minimum length of promoters required for tissue and developmental expression of genes in cotton.

Characterization of cotton promoters

In order to determine the minimum length of the promoter needed to direct fiber-specific expression of hetrologous genes in transgenic cotton we undertook the following experiments. A series of promoter fragments were constructed by progressive deletion of the 5' end of fiber-specific cotton promoters. Each of the deletion series were then tested for promoter activity by GUS transient expression assay, as described above. The fragments that retained promoter activity were then linked to a bacterial gene, acetoacetyl CoA reductase (also described above) and introduced into cotton by particle bombardment. Acetoacetyl CoA is an enzyme involved in the biosynthesis of polyhydroxybutyrate in bacteria. Expression of acetoacetyl CoA reductase was examined in fiber, leaf, stem, root and flower tissues of transformants.

The E6 gene family in cotton contains at least two members each in Sea Island and Coker cultivars (John, 1996, supra). The protein coding regions of E6 (E6-2A and E6-3B) from Sea Island show high homology. The E6 proteins share identical amino acid sequence (John, 1996, supra). Coker E6 genes, E6-1A and E6-4A, show some differences between them. The Coker E6-1A protein is 238 amino acid long while Coker E6-4A is 241 amino acid long. At the nucleotide level they are 99.4% identical. E6 genes from a related plant, cotton silk wood (Kapok, *Ceiba pentandra*) have also been analyzed and found to share homology with cotton genes (U.S. Pat. No. 5,495,070). The Kapok E6 protein coding sequence is 87% identical to cotton E6 at the nucleotide level.

The 5' region to the coding sequences of various E6 genes were sequenced and compared to each other. The following sequences are examined in this Example:

1) Sea Island E6-3B, SEQ ID NO:1 (2659 bp)
2) Coker E6-1 A, SEQ ID NO:2 (2755 bp)
3) Coker E6-4A, SEQ ID NO:3 (2539 bp)
4) Kapok CPE6-1A, SEQ ID NO:4 (2782 bp)
5) Sea Island FbLate2, SEQ ID NO:5 (2317 bp)
6) Sea Island SIB8, SEQ ID NO:6 (2168 bp)

Each of these sequences represents the 5' upstream region directly following the putative translation initiation site. Nucleotide sequences of the E6 genes 5' to the coding regions were compared to each other by the Bestfit computer program to assess the relatedness. These comparisons show that Coker E6-1A and Coker E6-4A sequences are 94.8% identical over a 2000 bp region. Thus these two sequences are considered homologous.

When the Kapok E6 ( CPE6-1A) sequence was compared to Coker E6-1A sequence a 70.3% identity was obtained over a 368 bp region immediately upstream of the coding region.

Deletion series of cotton E6-3B promoter.

FIG. 1 shows restriction maps of the deletion series of E6-3B promoters E6-2.7, E6-1.9, E6-1.2 and E6-0.3 kb fragments.

Each of these promoters were linked to GUS genes and introduced into cotton seed axes through particle bombardment as follows:

a. Construction of GUS gene with E6-2.7 kb promoter

Plasmid p2119 is a puc vector containing a 35s-GUS gene, Nos poly(A) addition signal and an AMV 5' untranslated leader sequence. This gene is functional in transgenic cotton. In order to construct a GUS gene with E6-2.7 kb promoter, p2119 was digested with HindIII/XbaI and the 2.2 kb promoter-less GUS fragment isolated by electrophoresis. Plasmid pE6-3B was digested with HindIII/XbaI and the GUS gene was ligated resulting in plasmid pE6-2.7GUS. The plasmid maps and construction of pE6-2.7GUS is shown in FIG. 2.

b. Construction of GUS gene with E6-1.9 kb promoter

The E6-2.7 kb promoter can be digested with Nsi to delete an 800 bp 5' end and obtain a 1.9 kb piece. For this an SK+ plasmid containing the E6-2.7 kb promoter was digested with Xho/Nsi and treated with T4 polymerase to blunt the ends. It was then religated to generate a vector containg the 1.9 kb promoter. A GUS gene was then added as a HindIII/SacI fragment to generate pB1498. The construct was bombarded into cotton seed axes to test for GUS expression.

c. Construction of GUS with 1.2 kb E6 promoter

Digestion of pE6-2.7GUS with EcoRI released a GUS gene and a 1.2 kb E6 promoter without a Nos poly(A) signal. The EcoRI fragment was cloned into an SK+ vector and a Nos poly(A) was added at BamHI/Xba site. The plasmid maps and construction are shown in FIG. 3.

d. Construction of GUS with 0.3 kb E6 promoter

A 209 bp fragment upstream of the initiation codon of E6 gene was amplified by PCR. Two primers MEJ661 and MEJ663 and pE6-3B DNA were used for PCR. The PCR product was digested with EcoRI and BamHI and ligated into SK+ vector, pSKE6-0.3. The vector was then linearized with Xba. A promoter-less GUS gene was excised from p2119 as a HindIII/Xba and Xba linkers were added after T4 polymerase treatment. The Xba GUS fragment was then ligated to pSKE6-0.3 plasmid. These steps are described in FIG. 4.

Each of these constructs described in FIGS. 2–4, along with control plasmids, were then introduced into cotton seed axes by particle bombardment and GUS activities were measured by MUG assays. These results are shown in FIG. 5.

The bar graph in FIG. 5 shows strong GUS expression from 35s-GUS plasmid (p2119). The three deletion series of E6 promoters, on the other hand, showed decreasing GUS activity as a function of decreasing length of the promoter. The 2.7 kb promoter was the strongest while the 0.3 kb the weakest. Though it appears that the promoter strength is lost when sequences upstream of 1.2 kb are deleted, stable expression data is required to confirm this observation. The experiment demonstrated that the minimum length required for promoter activity is 0.3 kb. Because the 2.7 and 1.2 kb E6 promoter fragments appeared to retain much of the promoter activity, we proceeded to link these two fragments as well as the 1.9 kb piece with acetoacetyl CoA reductase gene to generate stable transformants.

The E6-2.7, E6-1.9 and E6-1.2 kb promoter fragments were then linked to acetoacetyl CoA reductase genes and introduced into cotton. Following is the description of constructs containing E6 promoters linked to acetoacetyl CoA reductase gene.

e. Construction of pB1012 containing 2.7 kb E6 and acetoacetyl CoA reductase gene.

The Sea Island cotton E6 promoter (SIE6-3B) characterization is described in U.S. Pat. No. 5,495,070 (column 18–19). The promoter fragment is contained in vector pSKSIE6-3B. The 2.7 kb promoter fragment is sequenced and is disclosed in SEQ ID NO:1. The promoter fragment also contained the untranslated 5' leader sequence of E6 gene along with the ATG initiation codon of E6 mRNA. The promoter fragment was modified to remove the ATG of the E6 gene to facilitate the fusion with a coding sequence of transgenes and thus avoid translation initiation from the E6 ATG codon (E7-3B7P).

The acetoacetyl CoA reductase gene as a BamHI fragment was ligated to E6-3B7P and a poly A addition signal, Nos A, added as an Xba fragment. Marker gene 35s-GUS was added as Xho/Sal fragment. The construction of pB1012 is described in FIG. 6.

f. Construction of pBP923 containing E6-1.9 kb promoter and acetoacetyl CoA reductase gene.

The SK+ vector containing 1.9 kb promoter was digested with Cla/Sac and a reductase gene, along with Nos poly(A) addition signal from pB817, was added to generate pBP923.

g. Construction of pB1070 containing 1.2 kb E6-3B promoter and acetoacetyl CoA reductase gene.

DNA and other nuclear components within the nucleus are arranged in a highly ordered fashion. Nuclear organization is based on the proteinaceous nucleoskeleton and is called the nuclear scaffold. It is expected to play a role in nuclear processes such as replication, transcription and mRNA transport (Breyne, et al., *Transgenic Research* 3:195–202, 1994). The nuclear scaffold also provides anchoring sites for the genomic DNA. Such attachment of DNA to nuclear scaffold is mediated through specific DNA sequences called scaffold attachment regions (SAR). It has been suggested that SAR elements enhance stable gene expression in transgenic animals and plants (Breyne, et al., *Plant Cell* 4:463–471, 1992).

In order to test whether the SAR elements can enhance gene expression in cotton fiber we cloned a SAR element from yeast (Tschunper and Carbon, *Gene* 10:157–166, 1980). Two oligomers containing KpnI sites, 5'-CAGCGGTACCTCGAGCTGGTGGACTGACGC-3' and 5'-CGGCCTCGAGGTACCTGAAGGAGCATGTTC-3' (SEQ ID NOs:7 and 8) were used to amplify the SAR element. In addition, we also used primers with SacI sites to amplify the SAR element. The 800 bp fragments were purified and cloned into SK+ vector.

Figure 7:
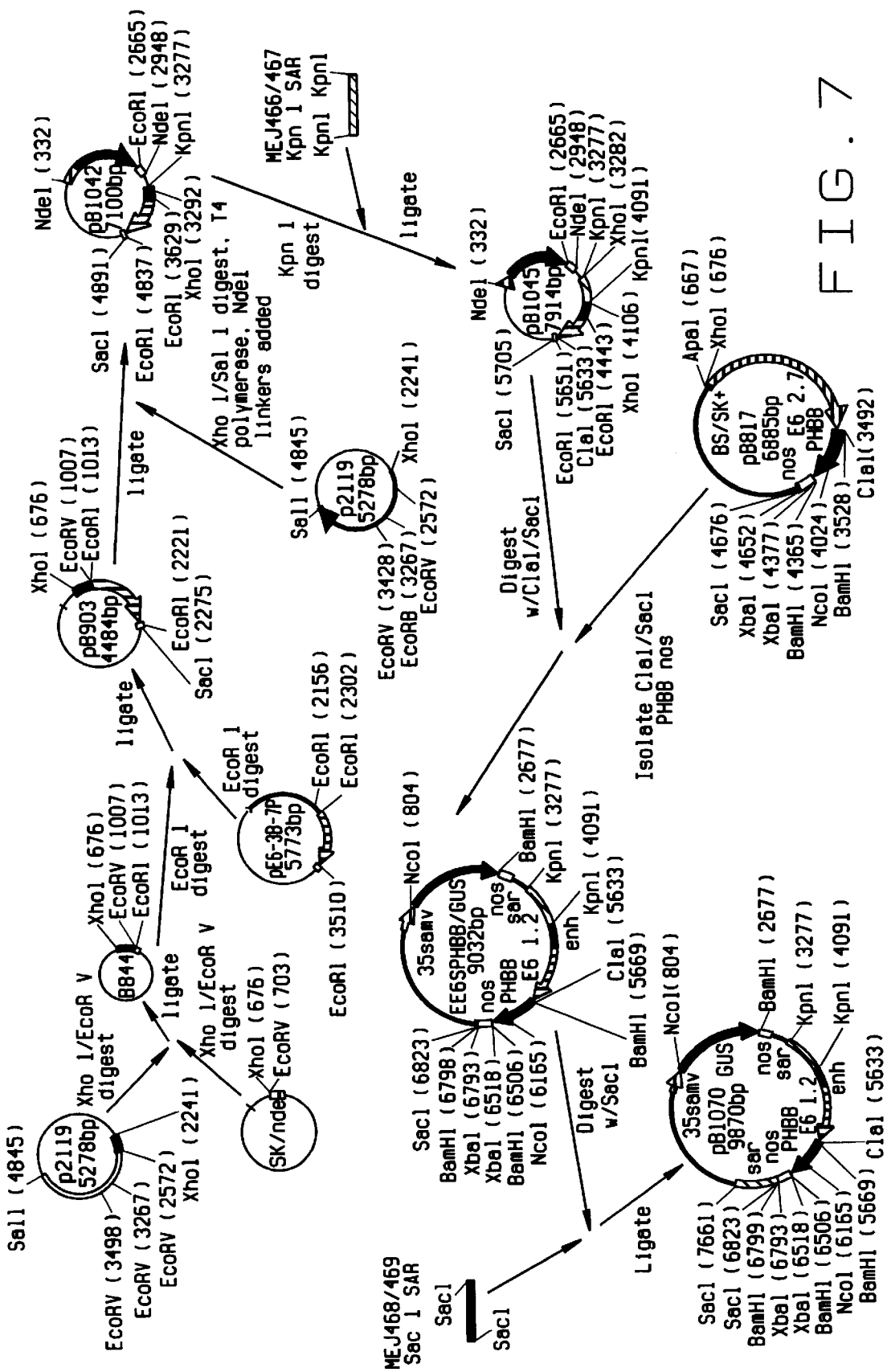
FIG. 7 is a diagram of the E6-3B-1.2 kb-acetoacetyl CoA reductase construction.

An acetoacetyl CoA reductase gene containing Nos(A) was linked to E6-1.2 kb promoter. A 35s-GUS gene was added to the construct. One SAR element each was added to 3' and 5' ends of the reductase gene. Details of the construct are illustrated in FIG. 7.

h. Expression of acetoacetyl CoA reductase gene in transgenic cotton containing E6 promoter deletion series.

Stable transformants were recovered for each construct and were screened for acetoacetyl CoA reductase activities in various tissues. Table 1 (see Appendix) shows typical example of reductase expression from plants containing the E6-2.7 kb construct. None of the plants showed reductase activity in leaf, flower, root or stem while fibers showed reductase activity. The pattern of reductase expression shows that it is developmentally regulated.

We recovered only one transformant (#13079) containing the E6-1.9 kb promoter linked to acetoacetyl CoA reductase gene. Various tissues of this plant was examined for reductase activity. Leaf tissue showed 0.194 μmol/min/mg activity while stem and flower tissue showed no activity. The bolls from this plant were aborting at about 5 days after flower opening and therefore activity in fiber could not be determined. However based on the fact that leaf tissue expressed reductase, we conclude that the 1.9 kb E6 promoter has lost its tissue specificity.

There is a possibility that during integration into cotton genome, part of the 1.9 kb E6 promoter may have been deleted and had therefore lost its tissue specificity. Thus, it was important to show that in the #13079 transgenic cotton plant, the 1.9 kb E6 promoter is intact and is linked to reductase gene. In order to prove this, we PCR amplified the E6 1.9 kb promoter from the DNA of #13079. A series of PCR primers were designed for the 5' end of the 1.9 kb promoter and the 3' end primer were designed to hybridize to the 5' end of reductase gene. This set up avoided the possibility that the PCR amplification will occur from the endogenous E6 promoter. In a series of experiments we showed that the 1.9 kb E6 promoter in #13079 is intact and is linked to reductase gene. Thus we conclude that 1.9 kb E6 promoter has lost its tissue specificity.

A number of transformants containing the deleted E6 promoter (1.2 kb) were examined and the results are shown in Table 2 (see Appendix). As seen from Table 2, the transformants expressed reductase gene in leaf, flower, root and stem tissues. Thus E6-1.2 kb promoter has lost ability for tissue-specific expression. From this result we conclude that E6-3B promoter has a tissue-specific element situated between 1.9 and 2.7 kb regions.

i. Other members of the E6 gene family and the FbLate gene family.

E6 is a family of genes in cotton. Two other E6 genes EG-1A and E6-4A, were sequenced from Coker 312 and are disclosed in SEQ ID NOs:2 and 3 respectively. Earlier we have demonstrated that E6 is present in other members of family malvacease (John and Crow, 1992). Examples include Kapok, Roselle, and wild relatives of cotton such as *G. longicalyx, Hibiscus sabdariffia* and *G. somalense.*

Figure 8:
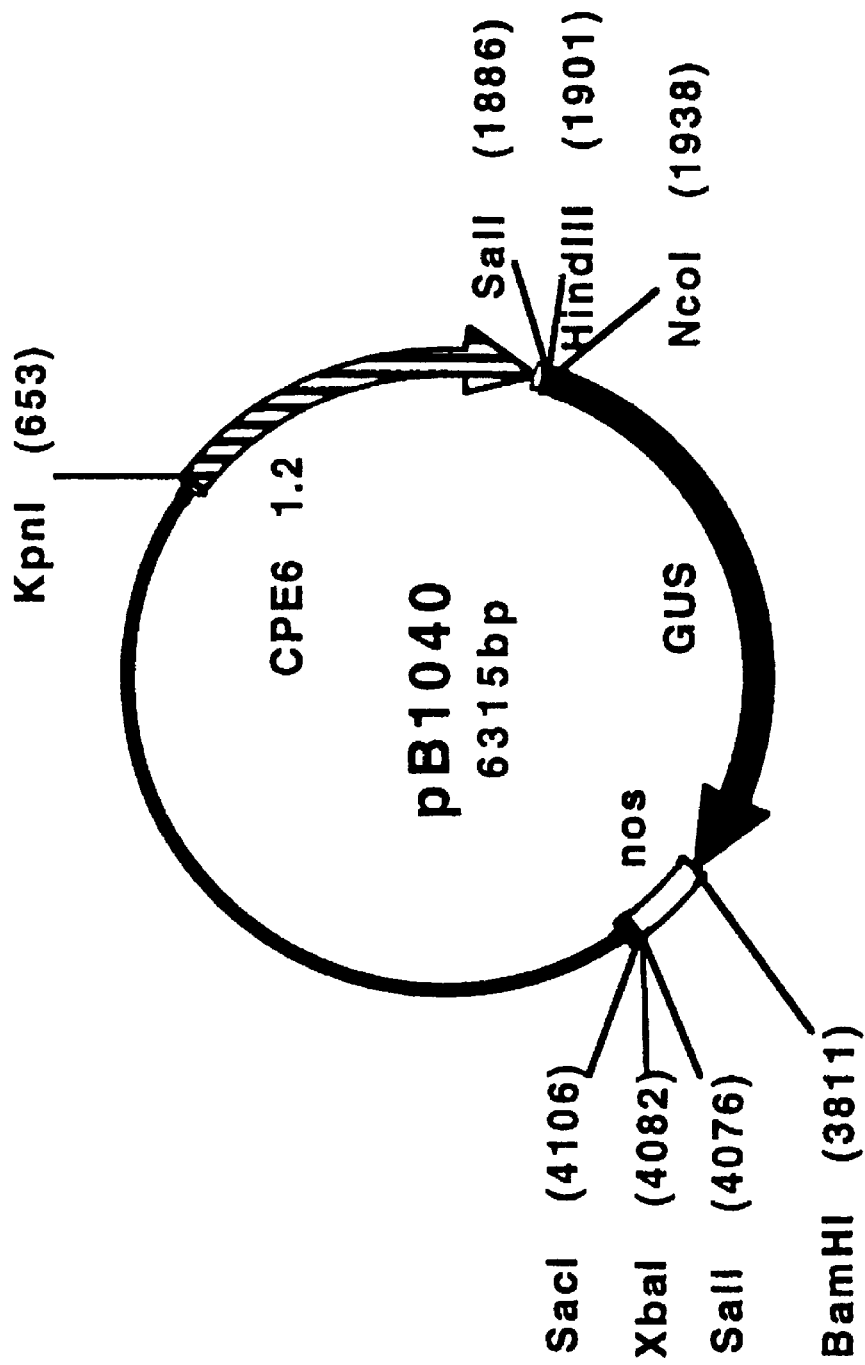
FIG. 8 is plasmid map of the Kapok 1.2 kb promoter linked to the GUS gene.

From Kapok we isolated two promoters that are 3.3 and 2.7 kb long by hybridization with cotton E6 gene. However, we have not introduced the 2.7 kb version to cotton yet. A 1.2 kb shorter version of the Kapok promoter was linked to acetoacetyl CoA reductase and introduced into cotton as follows. ( i) Construction of Kapok E6 promoter acetoacetyl CoA reductase gene The Kapok E6 gene is contained in SK+ vector, pCPE6-3A as a 15 kb fragment. The plasmid pCPE6-3A was digested with BamHI to remove a 5.3 kb fragment and then digested with NcoI. After treatment with mung bean nuclease to blunt end the Nco site, Sal linkers were added and religated (pCPE6-3A-Bam NCO). A 1.1 bp Kpn/Sal was excised and ligated to an SK+ vector containing AMV leader/GUS/Nos A to generate a 1.2 kb Kapok E6 promoter vector (pB1040). A restriction map of pB1041 is shown in FIG. 8.

Figure 9:
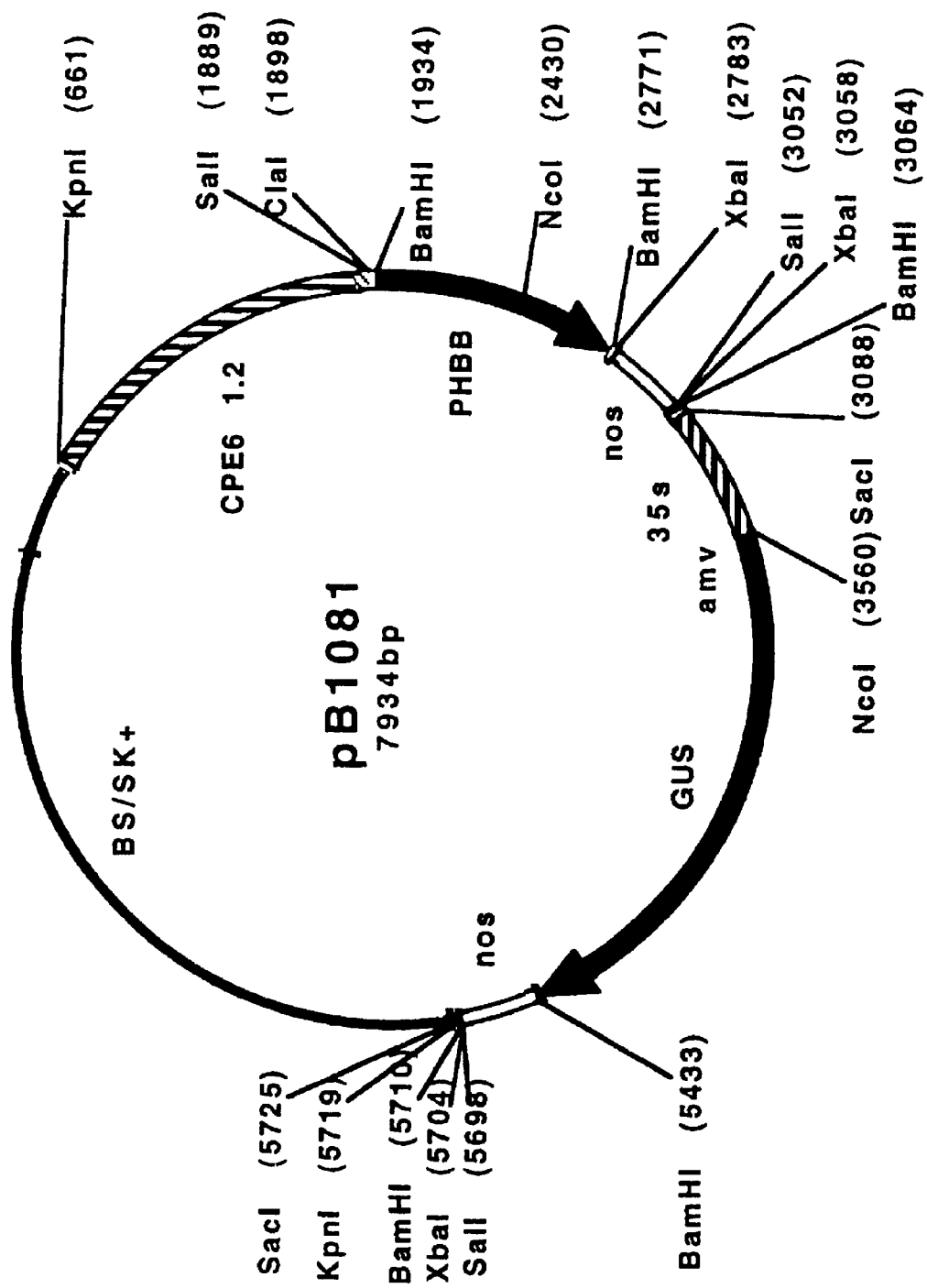
FIG. 9 is plasmid map of the Kapok 1.2 kb promoter linked to the acetoacetyl CoA reductase gene.

The Kapok 1.2 kb promoter was linked to acetoacetyl CoA reductase. The restriction map of the plasmid containing the promoter and gene is shown in FIG. 9.

Several transformants were recovered. We screened leaf, stem, flower, root, ovule and fiber tissues of these plants for reductase activity and the results are shown in Table 3. The short 1.2 kb Kapok promoter is not tissue specific. We speculate that a longer version of 2.7 kb is required for tissue specific expression. The 2.7 kb promoter is sequenced and is disclosed in SEQ ID NO:4.

(ii) FbLate2 deletion series

Figure 10:
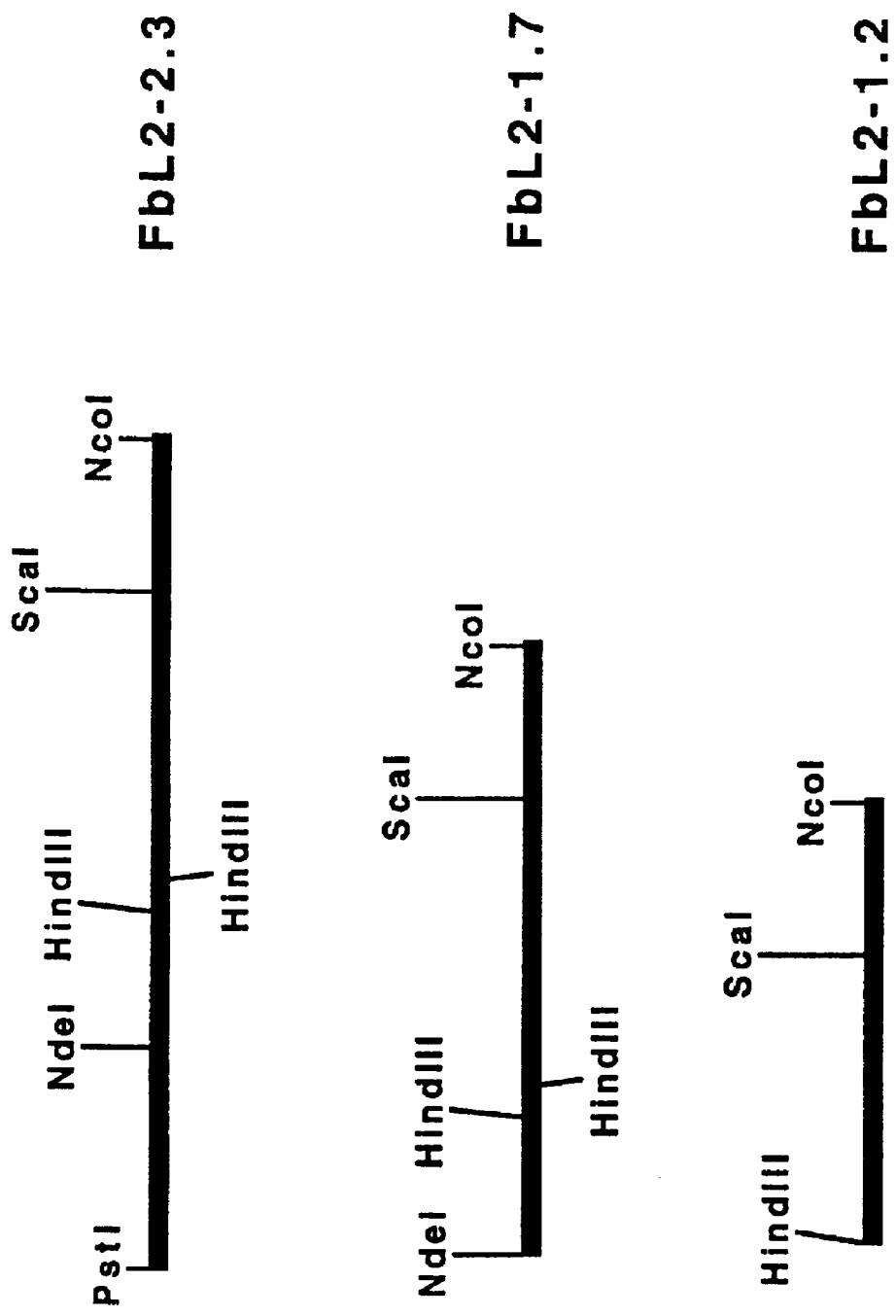
FIG. 10 is a restriction map of the FbLate2 promoter deletions.

A series of deletions were made from the 2.4 kb version of Fblate-2 promoter. The restriction maps of these fragments are shown in FIG. 10. Similar to E6 promoter we made GUS fusions with FbLate2 promoter fragments, the 2.3 kb, 1.7 and 1.2 kb. The plasmid constructs are described below.

Construction of FbLate2 GUS genes

Figure 11:
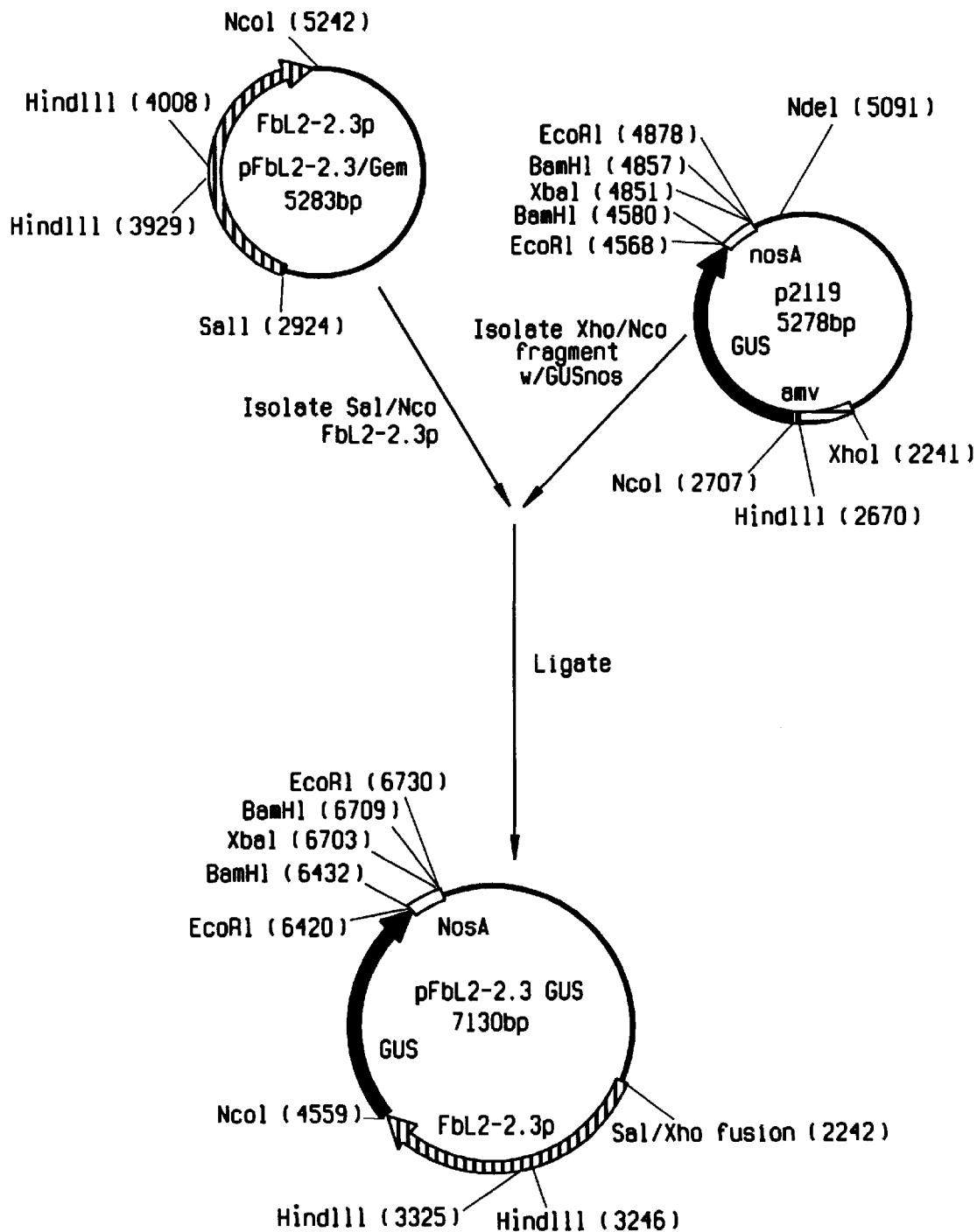
FIG. 11 is the construction of FbLate 2-2.3 kb promoter linked to GUS gene.

Plasmid pFbLate2-2.3 contains a 2.3 kb FbLate2 promoter. A 1.2 kb 3' fragment of the promoter was excised by digestion with HindIII/Nco and ligated to HindIII/Nco of an SK vector containing a promoter-less GUS gene. The plasmid maps and constructions are described in FIG. 11.

These constructs were then introduced into cotton seed axes and transient GUS expression was measured. The results are shown in FIG. 9.

Figure 12:
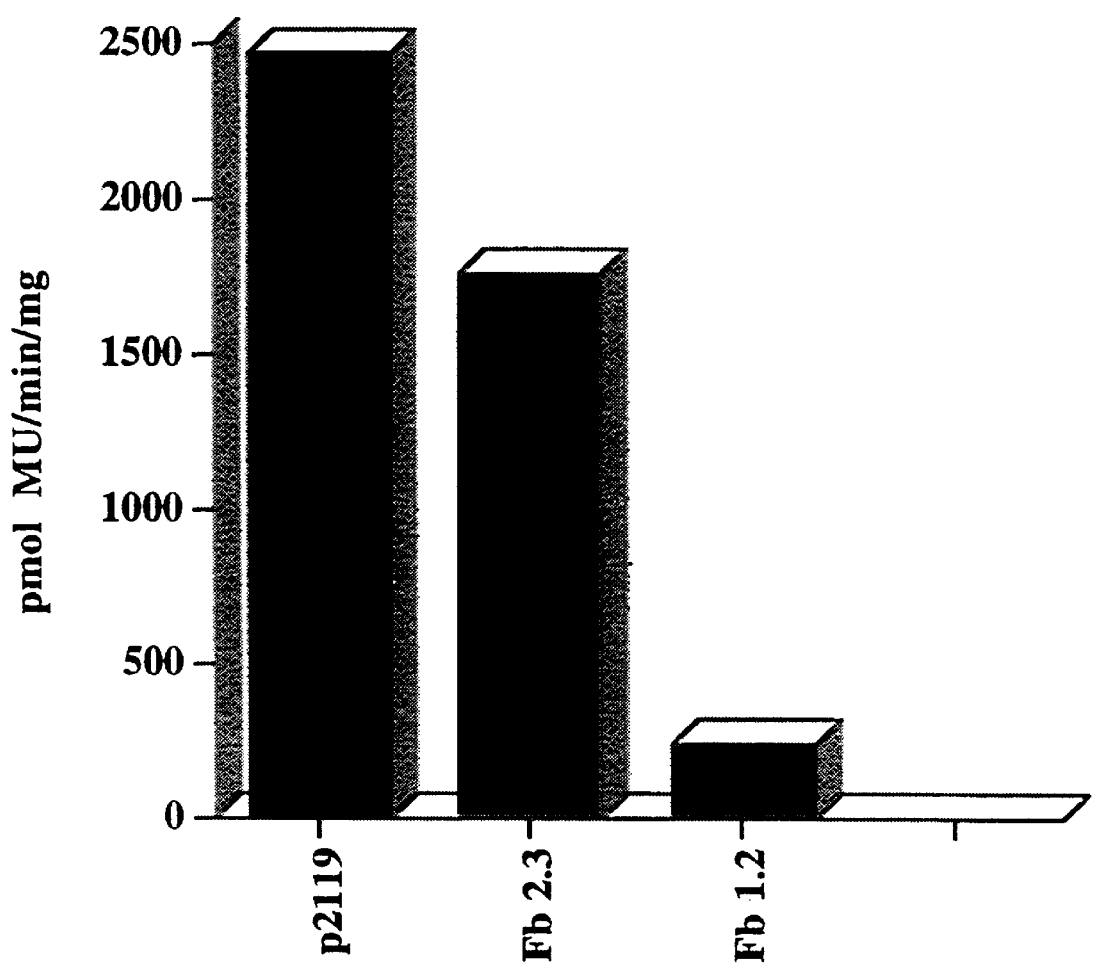
FIG. 12 diagrams the results of GUS expression from the FbLate2 promoter deletion series.

FIG. 12 shows the transient expression of GUS in cotton seed axes directed by various FbLate2 promoter fragments. The 2.3 kb fragment appears to be the strongest while the 1.2 kb is the weakest. We also made a GUS fusion with a 4 kb NcoI fragment that includes the 2.3 kb FbLate2 promoter. Transient expression from this gene construct was 1165 pmol/min/mg (not shown). Thus, we assume that the 1.2 kb fragment is sufficient for promoter activity. However, as seen from transient data the 2.3 kb version may have higher promoter strength. The FbLate2-2.3 kb was sequenced and is shown in SEQ ID NO:5.

Three of the fragments, FbLate2-2.3, 1.7 and 1.2 were then linked to the acetoacetyl CoA reductase gene and the constructs introduced into cotton as follows.

Construction of FbLate2 deletion series promoters linked to acetoacetyl CoA reductase.

Figure 13:
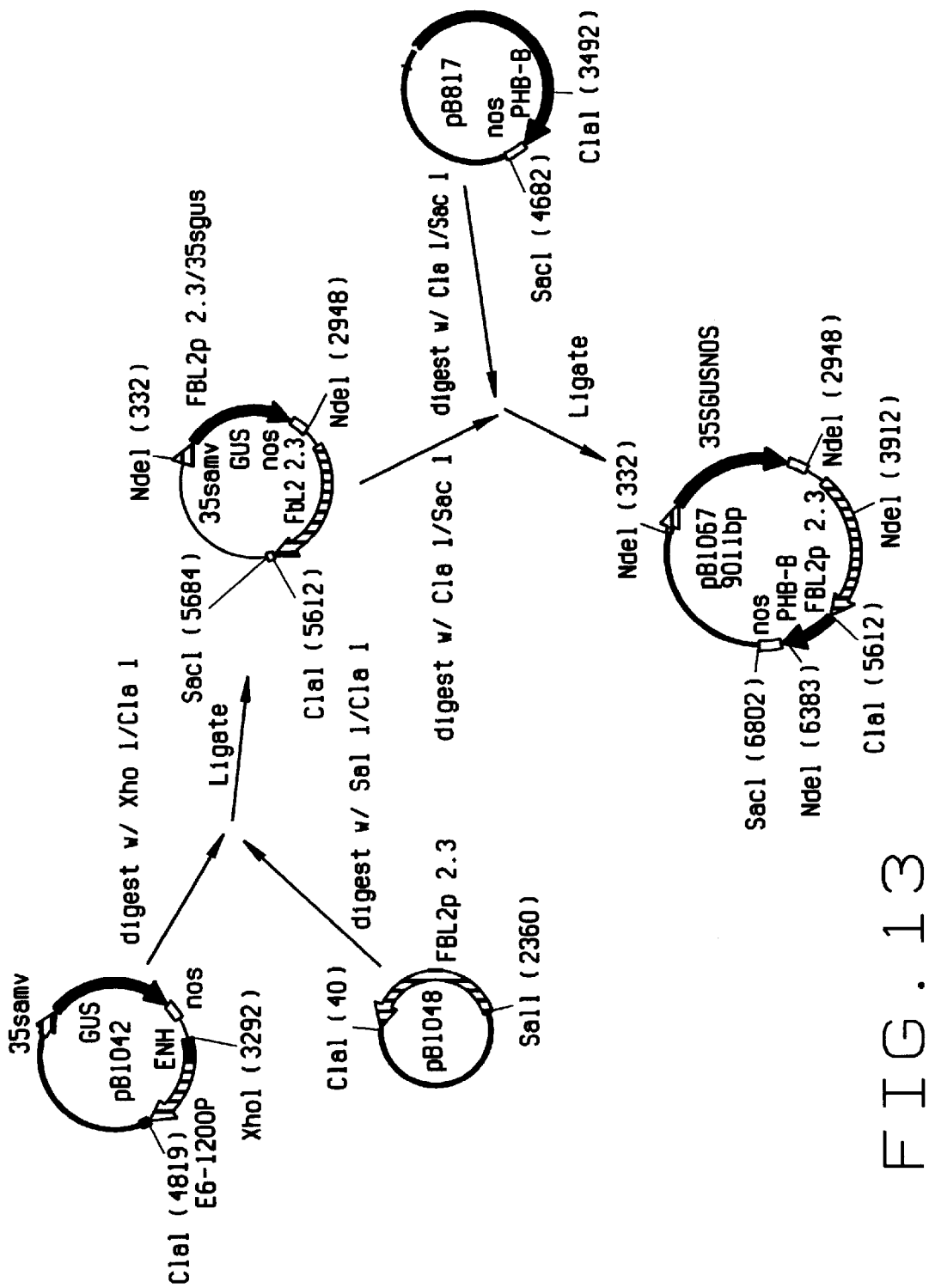
FIG. 13 is construction of FbLate 2-2.3 kb promoter linked to acetoacetyl CoA reductase.

The FbLate2-2.3 kb was excised from vector pB1048 as a Sal/ClaI fragment and gel purified. The promoter piece was then ligated to Xho/Cla site of plasmid pB1042 containing a 35s-GUS gene (FbL2-2.3/35s-GUS). The reductase gene was excised from pB817 and ligated to the Cla/Sac site of FbL22-2.3/35s-GUS to generate pB1067. These constructions are illustrated in FIG. 13.

Figure 14:
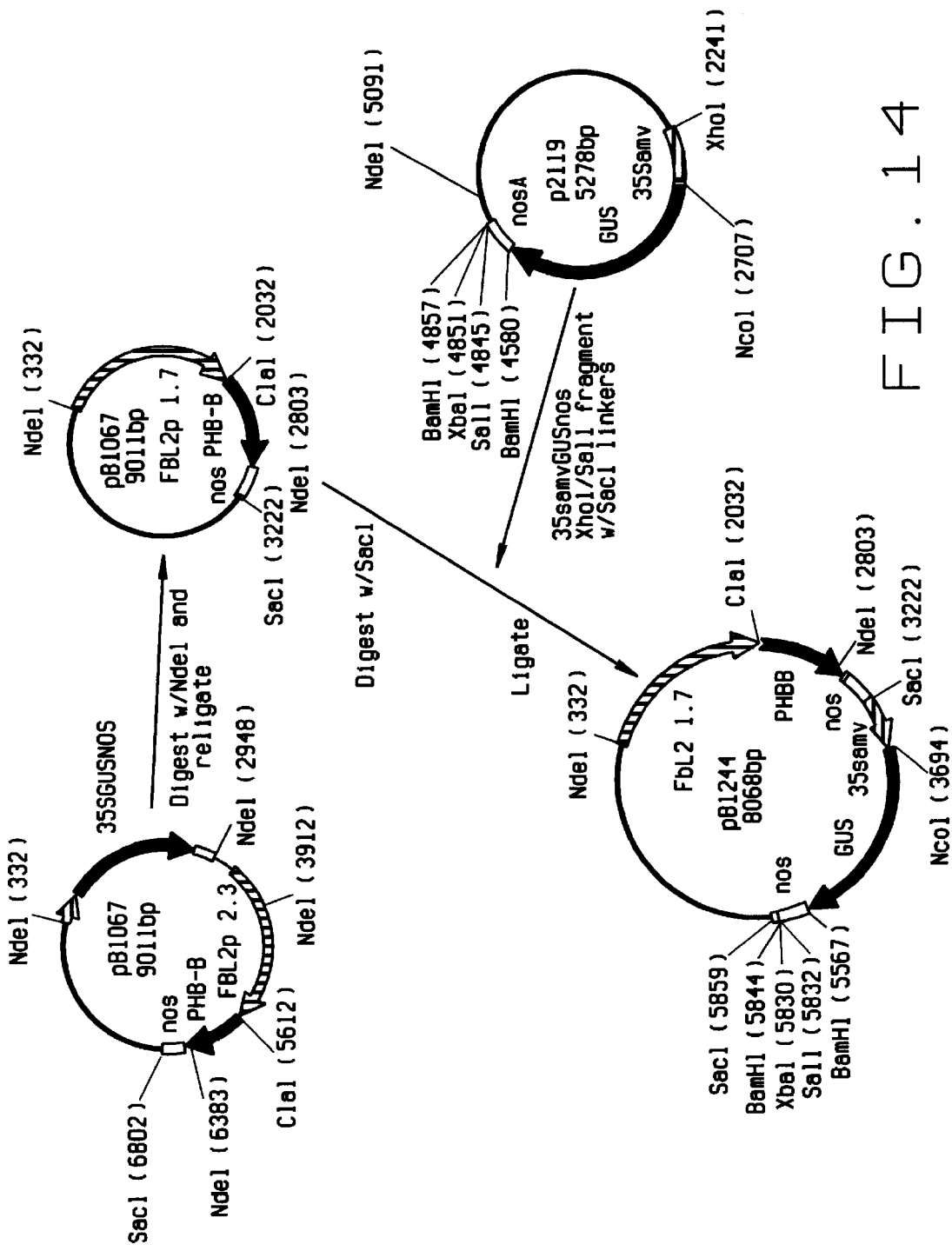
FIG. 14 is construction of FbLate 2–1.7 kb promoter linked to acetoacetyl CoA reductase.

Plasmid pB1067 was digested with NdeI and religated to generate a 1.7 kb FbLate2 promoter fragment linked to reductase gene (pB1212). Additionally the 35s-GUS gene was also removed. A 35s-GUS gene was added at SacI to generate pB1244 and is shown in FIG. 14.

Figure 15:
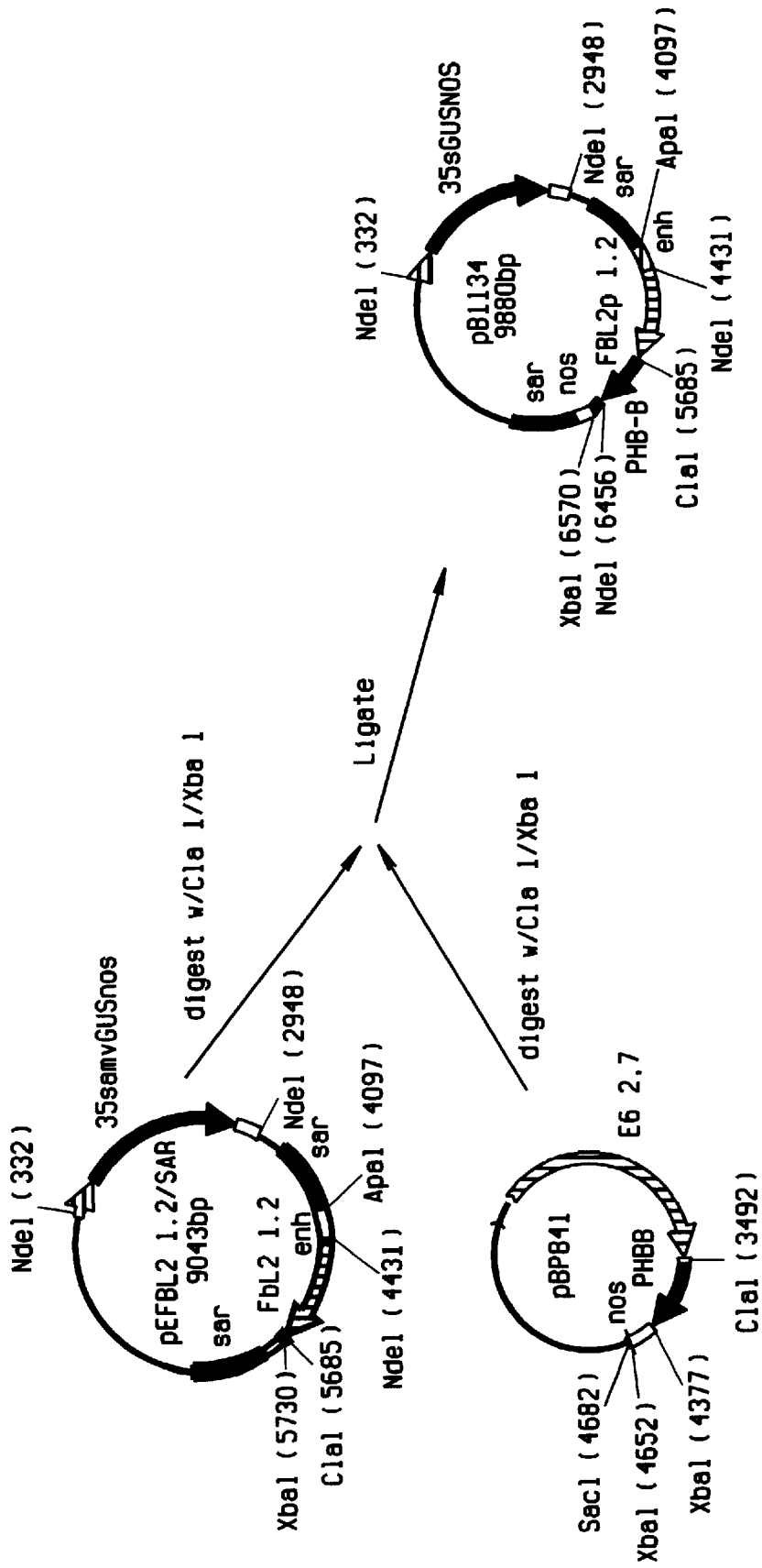
FIG. 15 is construction of FbLate 2–1.2 kb promoter linked to acetoacetyl CoA reductase.

A 330 bp Xho/EcoRV enhancer element was added to SK+ vector along with the 1.2 kb E6 promoter. The marker gene 35s-GUS was added as a Nde fragment. The 5' SAR element was added as Kpn/Kpn fragment and the 3' SAR was added as a Sac/Sac fragment. The poly A addition signal was added as a blunt end fragment at the BstXI site after T4 polymerase treatment. The E6 promoter was then replaced with FbLate2-1.2 kb fragment (pB1134, FIG. 15).

Stable transformants were recovered and screened for reductase enzyme and the results are shown in Tables 4, 5 and 6 (see Appendix). Table 4 shows the transformants containing the full length FbLate2 promoter. Leaf, stem, flower tissues do not show reductase activities, where as fibers show reductase activity. The full-length Fblate 2 promoter retains developmental regulation. Table 5 shows one transformant containing the 1.7 kb version of Fblate2 promoter. Leaf, stem and flower tissues did not show reductase activity whereas fibers showed enzyme activity. Table 6 shows transformants containing the 1.2 kb version of Fblate2 promoter. The transformants express reductase in leaf and stem. This result suggests that the Fblate-2 1.2 version has lost a fiber-specific element. However, the promoter does retain the characteristic developmental regulation.

Construction of SIB8 promoters linked to acetoacetyl CoA reductase genes.

We isolated the B8 gene promoter from a genomic clone and characterized a 2.2 kb BamHI/BstBI fragment. This fragment was able to direct expression of GUS in transient assay system. The isolation and characterization of B8 cDNA, gene and promoter were described in U.S. Pat. No. 5,495,070. The 2.2 kb B8 promoter was sequenced and is shown in SEQ ID NO:6.

In order to construct an acetoacetyl CoA reductase gene, we isolated the reductase from pE6-2.7-Red and linked it to B8 vector as a Cla/Sac fragment. Marker gene GUS was added to the construct to generate pB799. The plasmid map of B8-2.2 promoter linked to acetoacetyl CoA reductase gene is described in FIG. 16.

Figure 16:
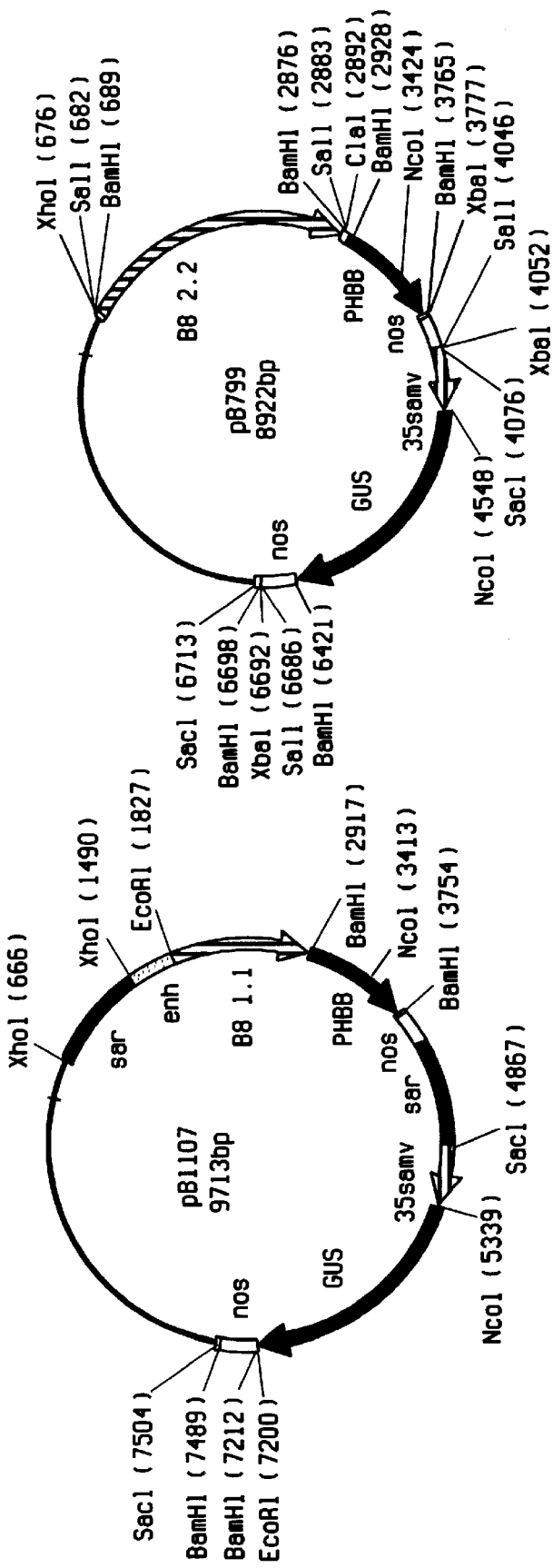
FIG. 16 is plasmid map of the B8 gene 2.2 kb and 1.1 kb promoters linked to the acetoacetyl CoA reductase genes.

The B8-2.2 promoter was restricted with HindIII and a 1.1 kb fragment was isolated and linked to SK+ vector. The 1.1 kb fragment was then excised as a EcoRI/BamHI fragment. A vector containing E6-1.2 promoter was digested with EcoRI and BamHI to remove the E6 promoter and the B8 promoter was ligated in its place. The reductase and GUS marker genes were added to generate pB1107. The plasmid map of pB1107 is also shown in FIG. 16.

We generated a limited number of transformants containing the B8-1.1 kb promoter and reductase gene. R1 progenies of one germline transformant was analyzed and the results are shown in Table 8. We detected reductase activity in stem, root and fiber indicating that the B8-1.1 kb promoter is not fiber-specific. We speculate that in order to obtain fiber specificity it is necessary to use a longer promoter, such as the 2.2 kb fragment.

As a positive control we used a constitutive promoter, cauliflower mosaic viral 35s late promoter linked to acetoacetyl CoA reductase. Transformants containing this gene construct is likely to express the gene in all tissues. Table 7 shows that leaf, stem and fiber tissues containing 35s reductase gene express reductase.

The results from all cotton promoters are summarized in Table 9. From these studies we conclude that the E6 promoters require the portion of the promoter situated between 1.9 and 2.4 kb from the start of the translation initiation for tissue specific regulation.

The region between 1.2 and 1.7 kb is required for tissue specific regulation of FbLate-2 promoter. Thus it is likely that there are tissue-specific elements located in the analogous regions of cotton promoters. Moreover, in majority of the transgenic plants carrying the FbLate2-2.3 kb promoter and acetoacetyl CoA reductase gene, the enzyme activity in fiber increased from 25–35-day, whereas in plants carrying the 1.2 kb version enzyme activity decreased from 25–35-day fibers. Thus, in addition to a tissue-specific element, there may be other DNA sequences that enhance transcription in conjunction with the tissue-specific element situated between 1.2 and 2.3 kb region of FbLate2 promoter.

j. Conclusions:
1) The region between 1.9 and 2.7 kb of the E6 promoter controls specificity of fiber expression, but not developmental regulation.
2) Based on sequence homologies of various members of E6 gene family in cotton and Kapok, we speculate that similar tissue-specific elements are present in the promoters of E6 genes. Moreover, it is likely that these elements are present in the region upstream of translation initiation codon approximately between 1.9 kb and 2.7 kb.
3) The region between 1.2 and 2.3 kb of FbLate2-A promoter controls fiber-specific expression. It is possible to narrow this further down to the region between 1.2 and 1.7 kb, even though more plants containing this shorter promoter need to be studied.
4) The region between 1.2 and 2.3 kb of FbLate2 promoter does not control developmental regulation of the gene expression, but may contain additional control elements that enhance transcription, in conjunction with tissue-specific element.
5) The B8 gene promoter is likely to direct fiber-specific transgene expression in cotton because we have shown that B8 gene expression is fiber-specific. Here we present evidence that a 1.1 kb B8 promoter does not confer fiber-specificity to transgene expression. Therefore, we speculate that a longer B8 promoter, such as the 2.4 kb fragment, confers fiber-specificity.

APPENDIX 1: TABLES 1–9

TABLE 1

Reductase Activity (E6 2.7 kb Promoter)

| | μmol/min/mg | | | | Fiber | | | | | |
|---|---|---|---|---|---|---|---|---|---|---|
| Plant # | Leaf | Stem | Root | Flower | 5-DPA | 10-DPA | 15-DPA | 20-DPA | 25-DPA | 30-DPA |
| 5384 | — | — | | | 0.05 | 0.16 | 0.13 | 0.12 | 0.1 | |
| 4992 | — | — | | | | 0.07 | | | | 0.12 |
| 12720 | — | — | — | — | 0.14 | 0.14 | 0.09 | 0.07 | 0.06 | 0.06 |
| 12334 | — | | | | | 0.11 | 0.08 | 0.06 | 0.06 | 0.06 |
| 12406 | — | | | | | 0.05 | | | | |
| 12165 | — | | | | | | 0.09 | | | |
| 12265 | — | | | | | | 0.04 | | | |
| 12266 | — | | | | | | 0.05 | | | |
| 11882 | — | — | | | | 0.06 | 0.06 | 0.06 | 0.04 | 0.03 |
| 11890 | — | | | | | | 0.07 | | | |
| 11948 | — | | | | | | 0.09 | | | |
| 11904 | — | | | | | | 0.03 | | | |
| 5522-8 | — | — | — | — | | | 0.08 | | | |
| 5297-32 | — | — | — | | | | 0.108 | | | |

Footnote:
Total number of transformants generated = 100
Total number of positive transformants identified = 36
Plants shown are representative of population

TABLE 2

Reductase Activity (E6 1.2 kb Promoter)

| | μmol/min/mg | | | | Fiber | | | | | |
|---|---|---|---|---|---|---|---|---|---|---|
| Plant # | Leaf | Root | Stem | Flower | 10-DPA | 15-DPA | 20-DPA | 25-DPA | 30-DPA | 35-DPA |
| 10068 (2-8) | 0.25 | | ND | ND | 0.1 | 0.04 | 0.02 | 0.03 | 0.03 | ND |
| 9823 | 0.02 | | 0.002 | 0.004 | ND | 0.16 | | | | |
| 10046 | 0.02 | | 0.005 | | ND | 0.04 | | | | |
| 10053 | 0.06 | | | | ND | 0.06 | | | | |
| 11707 | 0.04 | | | | | | | 0.25 | | |
| 10068-8 | 0.1 | 0.06 | 0.23 | — | | 0.03 | | | | |

Footnote:
Total number of transformants generated = 21
Total number of positive transformants identified = 6

TABLE 3

Reductase Activity (Kapok 1.1 kb Promoter)
(μmol/min/mg)

| Plant # | Leaf | Root | Ovule | Stem | Flower | Fiber 15-DPA |
|---|---|---|---|---|---|---|
| 8740 | 0.16 | | | — | 0.02 | 0.04 |
| 8740-1 | 0.17 | — | — | 0.06 | — | 0.04 |
| 8673 | 0.30 | | | 0.11 | 0.08 | 0.01 |
| 8673-3 | 0.15 | — | — | 0.22 | — | — |
| 8678-3 | 0.08 | — | — | 0.13 | — | — |

TABLE 3-continued

Reductase Activity (Kapok 1.1 kb Promoter) (μmol/min/mg)

| Plant # | Leaf | Root | Ovule | Stem | Flower | Fiber 15-DPA |
|---|---|---|---|---|---|---|
| 8705 | 0.09 | | | | | |
| 8705-2 | 0.09 | — | — | 0.05 | | — |
| 8698 | 0.10 | | | — | | |

Footnote:
Total number of transformants generated = 24
Total number of positive transformants identified = 8

TABLE 4

Reductase Activity (Fb Late-2 Promoter 2.3 kb)

| | μmol/min/mg | | | Fiber | | | | | |
|---|---|---|---|---|---|---|---|---|---|
| Plant # | Leaf | Stem | Flower | 10-DPA | 15-DPA | 20-DPA | 25-DPA | 30-DPA | 35-DPA |
| 8801 | — | — | — | — | 0.03 | 0.37 | 0.37 | 1.53 | 2.92 |
| 10413 | — | — | — | 0.007 | 0.05 | 0.30 | 0.65 | 1.13 | 1.92 |
| 10605-11 | — | — | — | 0.02 | 0.01 | 0.09 | 0.64 | 0.51 | 0.98 |
| 11764 | — | — | — | 0.03 | 0.03 | 0.04 | 0.03 | 0.03 | 0.06 |
| 11693 | — | — | — | 0.02 | 0.02 | 0.19 | 0.27 | 0.24 | 0.18 |
| 11689-7 | — | — | — | 0.008 | 0.02 | 0.83 | 0.85 | 1.2 | 1.74 |
| 11689 | — | | | 0.01 | 0.02 | 0.42 | | | |
| 11730 | — | | | | | 0.19 | | | |
| 11693.18 | — | — | — | | | 0.29 | | | |

Footnote:
Total number of transformants generated = 16
Total number of positive transformants identified = 9

TABLE 5

Reductase Activity (Fb Late-2 Promoter 1.7 kb)

| | μmol/min/mg | | | Fiber | | | | | |
|---|---|---|---|---|---|---|---|---|---|
| Plant # | Leaf | Stem | Flower | 10-DPA | 15-DPA | 20-DPA | 25-DPA | 30-DPA | 35-DPA |
| 12290 | — | — | — | 0.02 | 0.09 | 0.20 | 0.50 | 0.32 | |
| 12309-5 | — | | | 0.02 | | | | | |
| 12309-11 | — | — | — | 0.01 | | 0.004 | | | |
| 12309-20 | — | — | — | | | 0.003 | | | |

Footnote:
Total number of transformants generated = 3
Total number of positive transformants identified = 2

TABLE 6

Reductase Activity (Fb Late-2 Promoter 1.2 kb)

| | μmol/min/mg | | | | Fiber | | | | | |
|---|---|---|---|---|---|---|---|---|---|---|
| Plant # | Root | Leaf | Stem | Flower | 10-DPA | 15-DPA | 20-DPA | 25-DPA | 30-DPA | 35-DPA |
| 10472 | | 0.03 | 0.02 | — | 0.12 | 0.44 | 0.26 | 0.86 | 0.80 | 0.59 |
| 10512 | | — | 0.01 | | 0.04 | 0.03 | 0.08 | 0.09 | 0.05 | 0.01 |
| 10481 | | 0.02 | 0.01 | | 0.04 | 0.06 | 0.18 | 0.21 | 0.2 | 0.17 |
| 10529 | | — | 0.03 | | 0.004 | 0.01 | 0.14 | 0.17 | 0.06 | |
| 10804 | | 0.02 | | | | | 0.75 | | | |
| 10788-6 | — | — | — | — | | | 0.108 | | | |
| 10801-8 | — | 0.01 | 0.03 | | | | 0.156 | | | |

Footnote:
Total number of transformants generated = 15
Total number of positive transformants identified = 7

TABLE 7

Reductase Activity (35s Promoter)

| Plant # | μmol/min/mg | | | | Fiber | | | | | | |
|---|---|---|---|---|---|---|---|---|---|---|---|
| | Leaf | Flower | Root | Stem | 5-DPA | 10-DPA | 15-DPA | 20-DPA | 25-DPA | 30-DPA | 35-DPA |
| 12350 | 0.52 | | | | | | 0.008 | | | | |
| 12347 | 0.8 | | | 3.6 | 0.27 | 0.30 | 0.14 | 0.24 | 0.10 | 0.18 | 0.1 |
| 12659 | 0.03 | | | — | | | 0.02 | 0.03 | 0.02 | 0.02 | |
| 12352 | 0.03 | — | | — | | | | | | | |
| 12353 | 0.40 | | | — | | | | | | | |
| 12429 | 0.6 | | | 0.04 | 0.14 | 0.4 | 0.3 | 0.4 | 0.3 | | |
| 12068 | 0.009 | | | | | | — | | | | |
| 12071 | 0.01 | | | | | | — | | | | |
| 12350-1 | 1.001 | | 0.78 | 1.2 | 0.16 | 0.22 | 0.76 | 0.67 | 0.45 | 0.41 | |
| 12350-2 | 0.85 | — | | | | | | | | | |
| 12524-2 | 0.80 | | 0.40 | 0.64 | 0.17 | 0.23 | 0.67 | | | | |
| 12524-5 | 1.23 | | | | | | 0.49 | | | | |
| 12347-2 | 0.73 | | 0.25 | 0.16 | | | 0.28 | | | | |
| 12347-15 | 0.3 | | | | | | | | | | |
| 12656-13 | 0.19 | — | 0.26 | 0.07 | 0.008 | 0.21 | 0.20 | 0.20 | 0.21 | 0.22 | |
| 12656-12 | 0.30 | | | | | | 0.25 | | | | |
| 12350-2 | 0.85 | — | | | | | 0.56 | | | | |

Footnote:
Total number of transformants generated = 27
Total number of positive transformants identified = 15

TABLE 8

Reductase Activity (SIB8 Promoter 1.1 kb)

| Plant # | μmol/min/mg | | | | Fiber | | | | | | |
|---|---|---|---|---|---|---|---|---|---|---|---|
| | Stem | Flower | Root | Leaf | 5-DPA | 10-DPA | 15-DPA | 20-DPA | 25-DPA | 30-DPA | 35-DPA |
| 9882-22 | 0.131 | — | 0.02 | — | | 0.02 | 0.03 | 0.02 | 0.02 | 0.01 | |
| 9882-12 | 0.195 | — | 0.04 | — | | | 0.04 | | | | |
| 9882-32 | | | | | — | 0.02 | 0.02 | | | | |

TABLE 9

Summary of Deletion Studies of Cotton Promoters

| Promoter | Expression in Fiber | Developmental Regulation in Fiber | Expression in Other Tissues |
|---|---|---|---|
| E6-3B 2.7 kb | Yes | Yes | No |
| E6-3B 1.9 kb | ND | ND | Yes |
| E6-3B 1.2 kb | Yes | Yes | Yes |
| Fb Late-2 2.3 kb | Yes | Yes | No |
| Fb Late-2 1.7 kb | Yes | Yes | No |
| Fb Late-2 1.1 kb | Yes | Yes | Yes |
| Kapok E6 2.4 kb | ND | ND | ND |
| Kapok E6 1.1 kb | Yes | ND | Yes |
| B8-2.4 kb | ND | ND | ND |
| B8-1.1 kb | Yes | Yes | Yes |

ND = not done.

I claim:

1. An isolated fiber-specific promoter comprising at least 2.7 kb of the E6-3B promoter region of SEQ ID NO: 1.

2. An isolated fiber-specific promoter comprising at least 1.7 kb of the FbLate-2 promoter region of SEQ ID NO:5.

3. The promoter of claim 1 operably connected to a heterologous protein coding sequence.

4. The promoter of claim 2 operably connected to a heterologous protein coding sequence.

5. A fiber-producing transgenic cotton plant comprising a recombinant vector comprising at least 2.7 kb of the promoter region of SEQ ID NO: 1.

6. A fiber-producing transgenic cotton plant comprising a recombinant vector comprising at least 1.7 kb of the promoter region of SEQ ID NO:5.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 2659 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:1:

| | | | | | |
|---|---|---|---|---|---|
| CTCGAGGTCG | ACCTGCAGGT | CAACGGATCA | ACATTCAATT | ACAATAAAGA | GTATAGATAG | 60 |
| ATACATCAAT | ACTATCCAGC | CCTCTTTCAT | GATGATGTTG | CAAGTTTTGC | ACTCCACCCC | 120 |
| CATATTATTA | TGAAGAGGAG | AAATTCCTGT | TACAACATTA | ATTGAGCTTT | ATTTTCTAAG | 180 |
| AAATGACTTC | TAACATTAAT | AAATTTGAAT | CAATTTATAG | CTATTTCTCG | TACTCTTTCG | 240 |
| TAGTATAGCT | TTCTTTTTAT | GCTAAAACAG | GAGATGATTA | TAAGACGTGA | AGTTGTCTTA | 300 |
| AGATTAACAA | GGCAGTTAGA | TGCATTTAAA | TTGGTATTTA | AGGATATGTC | TGTATATAAC | 360 |
| TAGAACTAAT | TAAGATTACA | ATACACTGCA | AAATGATTCC | ACCTTTTTTT | TTTTTTTGGT | 420 |
| TCTCTCTTTT | ATATGATCAA | ATACAATGTT | GATATGAACA | AGGTTTTGCA | GTTGTAGAAA | 480 |
| ATCGTGGAGG | ACTTTTTTTT | TAAAAAAAGA | AAGATAAAAT | TCATAAAAAA | ATGTGAAGTT | 540 |
| AAGCATATTT | AGTGATGGGT | GGGGTATGGG | GTGGTTTGCT | AACATGGAAT | GCGCATGGCA | 600 |
| GATTGGCACT | TTAAAGAAGG | GATGGGGCCG | AGGGGCGGG | AGTTGTTAAA | TCCTCGGCGT | 660 |
| AGAAAAAGGT | CAGTAAGCGT | GTCCCTGGCA | TTAGACAAGG | AGAGGGGTA | GCACATGCAC | 720 |
| AGCCCAACTA | TATCTCTTTA | TTTTATGTCC | CACTCCACTC | CCCCTCATCT | CTGCCGCAAC | 780 |
| ATTAAATACC | TTATGCATCC | TTACTATTCA | TAATGGTTTT | TTTTGTTGGG | TTGATGTTAC | 840 |
| AAAATTAAAT | TTTTTATTAT | AGATGTATTA | ATATTTTTAA | AAATATATAA | GATTTTTTTT | 900 |
| AAGTAGGAGT | TTAATCTTTG | GTGGTGATGT | TGATTTTAGA | TATATTCCCC | ACCCGCAAGT | 960 |
| AGATATCATA | CATTCTAATA | TAATTTAAAA | AAAAGTATAA | CTAAAATATA | TTTTATATTT | 1020 |
| TTTTATATTT | TTTTGAATTT | TTAAATTTTA | AAAAATTAAT | TAAATGTTCA | TGTGTCATCT | 1080 |
| ACATGTATGC | AACGTTAGCG | AAGTTTAAAA | TATATTAATT | TTTTCATTCG | TGATTTGAAA | 1140 |
| AAAAAAAGGT | AAGTTTAAAG | GTTAAACAAG | CATAAATCTA | AATAAATAGT | TAAAATAATT | 1200 |
| TTTTTTATAA | AGTTAGAGAA | TTAAATAAAT | TATTATTTTA | TTTAAAAATA | ATTTTCAATA | 1260 |
| AATTACTAAT | TTAGTCACAT | AATCTAATAT | AATTTAAAAA | ATAATTATTA | ACATTTTAAT | 1320 |
| TTGTATGAAT | TCTTGTTATG | TATGGATTCA | AACCCGTTCG | TTCCATCAAC | AAATTGATCT | 1380 |
| GCATGAGACT | TAAGGGTTAG | AATTTTGTGT | AACCCTTTTT | CCTCCTAATT | TTTACTTTTA | 1440 |
| AAAAGAAATT | GCAATACAAT | TTTTTTTTTA | TAGAATTCTC | CTATTTTTAT | TTATTTATTT | 1500 |
| GCTTAGGAAG | TTTTACTGAC | ACTGCTTTTA | TTTTTCCATC | AATCAAATTT | AAGAGACAAT | 1560 |
| TCACTTTTTA | TAATTAACAA | AAAAAAACAA | AAAGAAAATA | AAAGAAATTA | CTTTTTTCTT | 1620 |
| TTTCGTGTTC | GATACAAGAT | AGATGAAATA | TGAAAAATAA | AATGAAATGA | AAATATATTA | 1680 |
| CTAGTGATAT | ATGACCTCCA | TTATGTAGGG | GAAAGAAATA | AAAATTATAT | TAATTTATGA | 1740 |
| TACTTCCATA | ATGTGGTTAA | AAATAATTAT | CTAGTATTTT | TTTGTAAAAA | AAAAAAGTT | 1800 |

```
GATATCTATG CTACTAATGA GGTTTCTTAG TGAGTTTGTT ACTACTAATA AAGTTTATTT      1860

GCATGGTTGA GACCTTATGC TTTTCAAATA CCCATATTTG AATTTTAAAA ATTGTGAATT      1920

TTTATTATAT TTAAAAAACA AGTTATTTAT ATAACTAGTA ATGTATTATT TTGACTTTTT      1980

TTTAATCGAG TTAATGTTGG TTATTTCGTT ATACCAATTC AATAAAATAT TTTATTTATA      2040

TTAAATTATA GCATACCTCA CGATGTGGGT GAAGTAAAAT TATTTAACAA ATATATTTTG      2100

AAAAATTGAT AAAAATACTA AATGAGGTTT TGGTTGAATA GTAAGATATA ATTATTACAA      2160

ATTATAAATA TGTAGGTTCA AAATCTATCA TGTGTATATT TGTACTATTA TTCTATATAA      2220

ATTGATAACC TTATAAAAGT ATCTAATTTA GTTTATGGTT GATTGATCGA TAATACCAAA      2280

TTTATTAAAA ATTAATATTA GTAAAGATAT ATAGTACAAA ACTAAACATA AAATTTTATA      2340

TGTTAAGGAA ATAGCGGAAA AAATATCATA TTTGTAGAAC TGTTTAGCAG TGTGGGAGAA      2400

TGGGATCATT ACAAGGAAAA ATGAAATATA TCATTAAT ACCAAACATA AAAGAAAGCG       2460

TCTTTTGATA AAGTTGTTAT TGGTGTAATG TGAAGGGACC ACAATCATCA CCATTCACCA      2520

CTTGCTCCTA ATTGAGTTGA AATCTTTTTA CAACATAGAA AACTAGAAGA TCGCCCTTTC      2580

TTGCTTCATA TATATAGATT TTGTATCATC GCAATTTCAC ATCACACACA CAAGTAAAGC      2640

ATTAGCAACC ATAGCCATG                                                   2659

(2) INFORMATION FOR SEQ ID NO:2:

(i) SEQUENCE CHARACTERISTICS:
         (A) LENGTH: 2755 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:2:

ATTGGAATAG TTGATTTCTT TCGAATATTA TTCGCTCAGT CGAGTAATGA GCTTCCGGTC        60

TTTGACTAAG ATGATCCCTT ATGTATGAAT ATAGGGGTTG GAATGTGAAG TAGGAATGAT       120

TTGAGAATAT GTATATTTGG AATTATCCGT TTAGTTATAT GAATGCCATA CTTCAATTGT       180

GCTTAATTTC ATTGCTCAAA ACTTACTAAG CATTAAATGC TTACTCCGTT CTATGAATTT       240

CTGTTTTATA GATTTTGGTT CGTCAGCTAT CGGACTAGGG ATTATTGAAG TCTCAGTCTC       300

CCACACTATC AAAGCCCTTT TTGGTACACT TTTGGTTGAA CTTTGAAATG GCATGTATAG       360

GACTATCCTT TTTGTTGTTG GTCATGGACC ATTTGGTTTT GTATAAATTT GGATAGCCAT       420

GCGAAAATGG CTTATATACA CTTTGAGCTT AATATTATAA TCGTCTTGTA TGATGTTCAT       480

TAAGAGGTAT GGAAATGTTT GGGAACGATT AGCCATTGGA ATGGTTAATC ATGATCAAAT       540

ACAATGTTGA TATGAACAAG GTTTTGCAGT TGTAGAAAAT CGTGGAGGAC TTTTTTTTTA       600

AAAAAGAAA GATAAAATTC ATAAAAAAAT GTGAAGTTAA GCATATTTAG TGATGGGTGG        660

GGTATGGGGT GGTTTGCTAA CATGGAATGC GCATGGCAGA TTGGCACTTT AAAGAAGGGA       720

TGGGGCCGAG GGGCGGGAG TTGTTAAATC CTCGGCGTAG AAAAAGGTCA GTAAGCGTGT        780

CCCTGGCATT AGACAAGGAG AGGGGGTAGC ACATGCACAG CCCAACTATA TCTCTTTATT       840

TTATGTCCCA CTCCACTCCC CCTCATCTCT GCCGCAACAT TAAATACCTT ATGCATCCTT       900

ACTATTCATA ATGGTTTTTT TGTTGGGTTG ATGTTACAAA ATTAAATTTT TTATTATAGA       960

TGTATTAATA TTTTTAAAAA TATATAAGAT TTTTTTTAAG TAGGAGTTTA ATCTTTGGTG      1020

GTGATGTTGA TTTTAGATAT ATTCCCCACC CGCAAGTAGA TATCATACAT TCTAATATAA      1080
```

-continued

```
TTTAAAAAAA AGTATAACTA AAATATATTT TATATTTTTT TATATTTTTT TGAATTTTTA    1140

AATTTTAAAA AATTAATTAA ATGTTCATGT GTCATCTACA TGTATGCAAC GTTAGCGAAG    1200

TTTAAAATAT ATTAATTTTT TCATTCGTGA TTTGAAAAAA AAAAGGTAAG TTTAAAGGTT    1260

AAACAAGCAT AAATCTAAAT AAATAGTTAA AATAATTTTT TTTATAAAGT TAGAGAATTA    1320

AATAAATTAT TATTTTATTT AAAAATAATT TTCAATAAAT TACTAATTTA GTCACATAAT    1380

CTAATATAAT TTAAAAAATA ATTATTAACA TTTTAATTTG TATGAATTCT TGTTATGTAT    1440

GGATTCAAAC CCGTTCGTTC CATCAACAAA TTGATCTGCA TGAGACTTAA GGGTTAGAAT    1500

TTTGTGTAAC CCTTTTTCCT CCTAATTTTT ACTTTTAAAA AGAAATTGCA ATACAATTTT    1560

TTTTTATAGA ATTCTCCTAT TTTTATTTAT TTATTTGCTT AGGAAGTTTT ACTGACACTG    1620

CTTTTATTTT TCCATCAATC AAATTTAAGA GACAATTCAC TTTTTATAAT TAACAAAAAA    1680

AAACAAAAAG AAAATAAAAG AAATTACTTT TTTCTTTTTC GTGTTCGATA CAAGATAGAT    1740

GAAATATGAA AAATAAAATG AAATGAAAAT ATATTACTAG TGATATATGA CCTCCATTAT    1800

GTAGGGAAA GAAATAAAAA TTATATTAAT TTATGATACT TCCATAATGT GGTTAAAAAT    1860

AATTATCTAG TATTTTTTTG TAAAAAAAAA AAAGTTGAT ATCTATGCTA CTAATGAGGT    1920

TTCTTAGTGA GTTTGTTACT ACTAATAAAG TTTATTTGCA TGGTTGAGAC CTTATGCTTT    1980

TCAAATACCC ATATTTGAAT TTTAAAAATT GTGAATTTTT ATTATATTTA AAAACAAGT    2040

TATTTATATA ACTAGTAATG TATTATTTTG ACTTTTTTTT AATCGAGTTA ATGTTGGTTA    2100

TTTCGTTATA CCAATTCAAT AAAATATTTT ATTTATATTA AATTATAGCA TACTCACGAT    2160

GTGGGTGAAG TAAAATTATT TAACAAATAT ATTTTGAAAA ATTGATAAAA ATACTAAATG    2220

AGGTTTTGGT TGAATAGTAA GATATAATTA TTACAAATTA TAAATATGTA GGTTCAAAAT    2280

CTATCATGTG TATATTTGTA CTATTATTCT ATATAAATTG ATAACCTTAT AAAAGTATCT    2340

AATTTAGTTT ATGGTTGATT GATCGATAAT ACCAAATTTA TTAAAAATTA ATATTAGTAA    2400

AGATATATAG TACAAAACTA AACATAAAAT TTTATATGTT AAGGAAATAG CGGAAAAAAT    2460

ATCATATTTG TAGAACTGTT TAGCAGTGTG GGAGAATGGG ATCATTACAA GGAAAAATGA    2520

AATATATATC ATTAATACCA AACATAAAAG AAAGCGTCTT TTGATAAAGT TGTTATTGGT    2580

GTAATGTGAA GGGACCACAA TCATCACCAT TCACCACTTG CTCCTAATTG AGTTGAAATC    2640

TTTTTACAAC ATAGAAAACT AGAAGATCGC CCTTTCTTGC TTCATATATA TAGATTTTGT    2700

ATCATCGCAA TTTCACATCA CACACACAAG TAAAGCATTA GCAACCATAG CCATG        2755
```

(2) INFORMATION FOR SEQ ID NO:3:

(i) SEQUENCE CHARACTERISTICS:
        (A) LENGTH: 2539 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
CTTTGCTTTT CTGTTTTTCC TTTGTTGATG GCGCCAAACG TAGTCTTAAA GTATATTAGA     60

TACATCTGGT GACCAACATT CAATTACAAT AAAGAGTATA GATAGATACA TCAATACTAT    120

CCAGCCCTCT TTCATGATGA TGTTGCAAGT TTTGCACTCC ACCCCCATAT TATTATGAAG    180

AGGAGAAATT CCTGTTAGTT GAGCTTTATT TTCTAAGAAA TGACTTCTAA CATTAATAAA    240

TTTGAATCAT GATATATTTA TAGCTATTTC TCTTACTCTC TCGTATTATA GCTTTCTTTA    300
```

```
TATGCTAAAA CAGGAGATGA GTAGGAAGAA ACAATTTTTG TTAAAAGACG TGAAGTTGTC    360

TTAAGATTGA CAAGGCAGTT AGATGCATTT AAATTGGTAT TTAAGGATAT GTCTGTATAT    420

AACTAGAACT AATTAAGATT ACAATACACT GCAAAATGAT TCCACCTTTT TTTTTGGGGG    480

GTTCTCTCTT TTATATGATC AAATACAATG TTGATATGAA CAAGGTTTTG CAGTTGTAGA    540

AAATCGTGGA GGACTTTTTT TTTACAAAAA AGAAAGATAA AATTCATAAA AAAATGTGAA    600

GTTAAGCATA TTTAGCGACG GGTGGGGTAT GGGGTGGTTT GCTAACATGG AATGCGCATG    660

GCAGATTGGC ACTTTAAAGA AGGGATGGGG CCGAGGGGGC GGGAGTTGTT AAATCCTCGG    720

GGTAGAAAAA GGTAAGTAAG CGTGTCCCTG GCATTAGACA AGGAGTAGAG GGGGCAGCAC    780

ATGCACAGCA TAACTATATC TCTTTATTTT ATGTCCCACT CCACTCCCCC TCATCTCTGC    840

CGCAACATTA AGTACCATAT GCATCCTTAC TATTCATAAT GGTTTTTTGT TGGGTTGATG    900

TTACAAAATT ACAATTTTAC TATAGATGTA TTTATAATAT TTAAGATTTT TTTAAGTAGG    960

AGTTTAATCT TTGGTGGTGA TGTTGATTTT AGATATATTC CCCACCCGCA AGTAGATATC   1020

ATACATTCTA ATATAATTAA AAATGGTATA ATTAAATATT TTTTAATATT TTTAATATTA   1080

TTTTTATATT TTTTGAATTT TTAAATTTTA AAAAATTAAT TAAATTTTGA TGCGTCATCT   1140

ACATGTATGC AACGGCGAAG CTTAAAAAAT ATTAATTTTT TTCATTCGTG ATTTGACAAA   1200

AAAAAGTAAG TTTAAAGGCT AAAAAAGCAT AAATTTAAAT AAATAGCTAA ATAATTTTT    1260

TTACAAAGTT AGAGAGCTAA ATAAATTATT ATTTTATTTA AAAATATTTT TTTAATAAAT   1320

TATTAATTTA GTCACATAAT CTAATATAAT TTAATTCAAA CCCGTTGGTT CCATCAACAA   1380

ATTGATCTGC ATGAGACTTA AGGGTTAGAA TTTGGTGTGT AACTCTTTTT CCTCCTAATT   1440

TTTACTTTTA AAAAGAAATT GCAATACAAT TTTTTTATTA TAGAATTCTC CAATTTTTAT   1500

TTATTTATTT GATCAGGAAG CTTTATTGAC ACTGCTTTTA TTTTTCCATC AATCCAATTT   1560

AAGAGACAAT TCACTTTTTA TAATTAACAA AAAACAAAAA GAAATAAAA GAAATTACTT    1620

TTTCCTTTTT CGTGTTCGAT ACAAGATAGA TGAAATATGG AAAATAAAAT GCAATGAAAA   1680

TATATTATTA GTGATATATC ACCTCCATTA TGTAGGGGAA AGAAATAAAA ATAATATTAA   1740

TTTATGATAC TTTCATAATG TGGTTAAAAA TAATTATCTA GTATTTTTTT GTAAAAAAAA   1800

AGAAAGTTGA TATCTATGCT ACTAATGAAG TTTCTTAGTG AGTTTGTTAC TAATCATATT   1860

CGAATTTTAA AAATTGTGAA TTTTTAAAAA ATAAGTTATT TATATAACTA GTAATATACT   1920

ATTTTGACTC TTTTTTTATC CGAGTTAATG TTAGTTATCT CGTGATACCA ATTCAATAAA   1980

ACACTTTATT TATATTAAAT TAATATAGCA TACTGGGTGA GAAGTAAAAC TATTTAACAA   2040

ATATATTCTT AAAAATACTA AAGGAGGTTT TGGTTGAATA GCAAAATATA AATATTACAA   2100

ATTATAAAAA TGTAGGTTCC AATATTTTTA CTATTTTTCT ATATAAAATG ATAACCTTAA   2160

AAAGTAGTTT GTGGTTGATG GACTAATTTT TTAAAAAGAA TTAATATTAG TAAAGATATA   2220

TATGGTACTA AACATAAGGA AATAGGGAAA ACGTATCATA TTTGTAGTGG GAGAATGGGA   2280

TCATTACAAG GAAAAATGAA ATACATATCC TTAACAACAA ACATAAAAGA AAGCGTCTTT   2340

TGATAAAGTT GTTATTGGTG TAATGTGAAG GGACCACAAT CATCACCATT CACCACTTGC   2400

TCCTAATTGA GTTGAAATCT TTTTACAACA TAGAAAACTA GAACATCTCC CTTTCTTGCT   2460

TCCTATATAT AGATTTTGTA TCATCGCAAT TCCACATCAC ACACGCAAGC AAAGCAAAGC   2520

ATTAGCAACC ATAGCCATG                                                2539
```

(2) INFORMATION FOR SEQ ID NO:4:

```
    (i) SEQUENCE CHARACTERISTICS:
        (A) LENGTH: 2781 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

TGCTAATGTG AAGTATATAT TCATTTGTCA TCTCCAATCC TCTCATCCTA AAAAGCTAAT      60

ATTATATAAA CTTTCATGTC TTCATCAAAG AGTTGGCGTC CCTAGACTAG ACTTGGAGTC     120

GTACTTTCAT GTTCTTGGCT ATGCAAAATT TAAACTTAAC GTTTTTATCC CCTTTTTTTC     180

GTTGTTATTA TGTTTATTTT GTGGTTTAGC CATTGGTGTA TGAATTTTAA TTGCATGAAT     240

CACAAAGGGG CATGAGTCAA ATATCATTGT GAAGAGAAGT GTCTTTGTCC TTTTTAACTT     300

TCCTTTTCTT TGTTTCTTTT TTTTTTTTTT TAATTTTTCC CTTTGATATT GGCGATATTC     360

ATATTAAAGC TTATTAAAAA CATTTGGTAA CCGATATTCA ATTACAATAA AGGAATATGA     420

TGTTGCAATT GCTAGTTTTG CACTCTATGA ATTTTATGAA GCTTTAAATT GATATATAGA     480

TATATATATA TATATATATG TATAACATAT TTTGCATAGA GATTTTGACA TTGTCTCCTT     540

GCTTTTCTTT TCATTTTTTT TAATTCATCT TCAAAATTAG ATAATTAAGT AATACCAGTT     600

GCATGCATTT AAATTGGTAT TTAAGAATGG TGTGTGTCTC TTAAGGACTG AAAAAGATAA     660

TTATGAAAAA AAAATTGGTT ATCTAATGGT TAAATTACAA AATAGAAAAT GAATTATACA     720

TCTTAACCAT TGAAAATTAA CTTCTTTTTT TTTCTGTTCT TATGACTTCC ATCTTTCTTA     780

CCAAGTAAAC ATGACAAAGA AATTGAATTT TTCTCCATCA CGTTAATTAA TCAAATTTGA     840

ACTTAATATT TTTATTAAAG TGTCAAATTC CTTGAGTCAA AAATTTTATA TATAATTTGT     900

CAATCCAATT TCTTTCTTTC TTTTTTTTTT TTAATATGAA TACAGTATTG ATGAATTGAC     960

CAAGAGTTTT GCAAATGTAG AAAATCATAC CAGTCAGTGT ACTACCAAAA GAATTTCAAA    1020

AAGAAAATGA GAAGTTAGCA ATGAGTGGGG TTCCTTCGCA AATTATGCTT GGAACGCGCA    1080

TGGATTATGG CACTTTAAAG GAGGCAAGCA GCAGCTGAAA ATTTTATATG CAAGATGAAT    1140

ATGATATAAT AAAATAAATT AAAATATGAT ATTAATATAA TATAAAAATA AAAATAAATT    1200

AAAATTTATA TATAATATAT TATTAATATA TCAAAATTTA TAAAATATAA ATTATTTTAA    1260

ATATAATTAT AATATATATT AAAATATATA AATAAAATAA TATATAAAAT TTCGAATCTA    1320

AACTAAATAA CTATTAAATC CTGTGTGTGG AAAGGGGATG GTCCGTCCCT AATATTAGAC    1380

AAAGAATAGA GGGGGTGGCA CATGGAGAGA GAGAGAGAGA GAGAGAGAGC AAAGCTAAGC    1440

TTTATAGTCA TTATTTTATG TCCCACCAAT TCCCTCAATC CTCGCAATAT CACACGCCGT    1500

CCCCTTTCAT CTATTTCCAG TCTTTACCCA TTTCTACATT TTCTAAGCCT AAGGTACCCT    1560

ACCCTCTGTT CACAATGCTT CTATTTTCCC ATTAATCACA TGCATTTCCT GATAACATAC    1620

TTTTATTTAT ATATATATAT ATAATATAAT TAATCAGCTT TGAAATTAGA AGGTAGGAAA    1680

ATTGGAAAAG CCAAAAGAAA TGGAAAAAAA TTTCGATTTG AAATAAAGTT TAATTTAAAT    1740

GATTTATTTA TAATATCACT TCTCGTAAAA TTAAAATTTA ATTTTTAATG CTTGAATTTT    1800

TTTTTTCCAA ATCTCTTAAA CTCTAATAAA TTTCATACCA AAAAGGGAA AATTTGTTTT     1860

TTTTTTTTA ATTTTGATAT AGGAGAGATG ATAAATGAAA TAAGAAAAAT TAAAGTCGAA     1920

AAGAAATGAA ATTAATACTA AAATGAAGAA AATCTGGTAT CAAATTTGAT AAATTATTAG    1980

TAACATTTTA TACCCTTATA TCATCCAATA CAAACAAAAA TATTTTAATG GCTGCTACTA    2040
```

```
CTATGCCTTA ATATATTGGA ATAAGGCCAA TTTTGCTTTT GCTTAGAAAA TACGAAATAC      2100

TCATAAGAGT TTTATACAAA TGATAGGAAA CACGCTTTTT TTTTTCATAA ATCACGAAGG      2160

AATCTTGAGG AAAAATGCCA ACCCTTGTTT AACCTGTTTA CCACAGTGGG GAAAATGAGA      2220

TCATAAAGAA TCTGAGCCTG AGTAATTTTT AAATTTAATT TTTTTTTACA TTAGTTCGGA      2280

TTTATACACT GAATTAAAAT TAAATTTAAA TAAAAAATTT AAAGATATTT GAGAATGTCT      2340

CTACTTAATT TATGTAATGG TATTTAGTAT ATTTAAATTT TAAATATTAA TATATGTAAA      2400

ATTAAAAAAA AAAATTAGAT TAGGATTTAT TTTATAAAAA AAATGGAAAT GAGATCATAA      2460

AAAGAGCACC AAATAATAAT AATAAAAGAA GAAATCAAAG TCAATCATTA ACAACAAACA      2520

CAAAGTGAAG AGGCCACTTT TGATAAAGTC TTATGTCTCG TGCAAGGGAC CACACACACA      2580

ATCATCAGTT TTCACAGTCT CCCCCCCGTC CCGTTTGCAA CTAATTGAGT AGAAAATTTT      2640

ACAAATTGAG GGGAAACGAA AAAATTTGCC TTTCTATATA AACATTTCCT ATCATCACAA      2700

TTTCTCATTA GTGTGCACTC TCCCACGCAA AAAAAAAAA  AAAAAGAAAG AAAGCATTAG     2760

CTAGCCTTCC CCTTGCCCAT G                                                2781

(2) INFORMATION FOR SEQ ID NO:5:

(i) SEQUENCE CHARACTERISTICS:
        (A) LENGTH: 2317 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

CTGCAGACTT AGGATTGGAT GGCGTTCAGG AGCTTGGATT GGTTTTCTCA CATCATATTT        60

TATTAAATAA TTATTAATTA AAATTTATGG ACTTTTGGAC TGTCTGACTA ATTTTCAGAA       120

TTTTATTTTG GTTTTGGGTT TTGTTGAGTT TTTTAGATAA TTATTTTAAA TATTCTGCAT       180

AATTTTTCTG TTATTTGAAA AGGATGTTCG AATTTTTTTT CAAAATTGAA ACGTTTAAGA       240

ATTTTTACTA CTGCAAATTC AGAATAAGTG AATTTGTTTT TTAGAAAGAT TAAATAAGTT       300

AGTATTACGA TTTTTAGTTT GATTTGGTGG AAAGTAATGT ATGTTTTTGA ACATAATTAT       360

TTGACAATAA TTAAGTTTTC TAGGAAATAA ACGGAAATAT CTTCTTTTTT TTTTGTAAAA       420

TTACTAATGC AAGAACAAAC AACGTTTTGG GAAGCAAATA ATCTAGCTTT AAGTAGTCAG       480

TGTAACTCTC AAAATCTGGT CATAACTTCT AGGCTGAGTT TGCTGTGCTA CAGTAGTAAG       540

TCTATAGAAA CTTACCTGAC AAAACGACAT GACGTCAGGG TCGAATCTAC AACTTTTCCT       600

TTTTCTTCAA TTAACATATG GTTGATTCAA GTTCCGATCT ATAATAATTT ATTACGATTT       660

ATCAATTTCA ATTACCTTAT ATCATCCTAT TATAAATATA AGTCAGTTCA ATTCAGTTTT       720

CGAAAGTTCC CTAAAATTTT GAATTTTATT AAATTTATTC CCTAAAACCG AAATAGTGAT       780

ATCTTTCAAA TTTAAGTTTC ATTTTTCAAT CCGATTTCAA TTTCATCCTT TTATAACTCT       840

CTATGATCTA TAATTACATA AATTTCAAAC TAATTTTGAA ATATATACAC TTTAGTCCCT       900

AAGTTCAAAA CTATAAATTT TCACTTTAGA AATTAATCAT TTTTCACATC TAAGCATCAA       960

ATTTAACCAA ATGACACAAA TTTCATGATT AGTTAGATCA AGCTTTTGAG TCTTCAAAAA      1020

CATAAAAATT ACAAAAAAAA AAAAACAAAC TTAAAATCAT TTATCAATTT GAACAACAAA      1080

GCTTGGCCGA ATGCTAAGAG CTTAAAAATG GCTTCTTTTG TTTCTTTTTG TTGCAAACGG      1140

TGGAGAGAAG AGGGAAATGA AGATTGACCA TATTTTTTTA TTATGTTTTA ACATATAATA      1200
```

-continued

```
TTAATAATTT AATCATAATT ATACTTTGGT GAATGTGACA GTGGGAGAT ACGTAAAGTA      1260

TATAACATTA TACTTTTTGC AAGCAGTTGG CTGGTCTATC CAAGAGTGAT CAAAGTTTGA      1320

GCTGCCTTCA ATGAGCCAAT TTTTGCCCAT AATGGATAAA GGCAATTTGT TTAGTTCAAC      1380

TGCTCACAGA ATAATGTTAA AATGAAATTA AAATAAGGTG GCCTGGTCAC ACACACACAA      1440

AAAAAAAACT AATGTTGGTT GGTTGAATTT TATATTACGG AATGTAATGT TATATTTTAA      1500

AATAAAATTA TGTTATTTAG ATTCTTAATA TTTTGAGCAT TCCATACTAT AATCTCGTAT      1560

ACATAATATT AAAATATAGT AATATAAAGT GTAATTAACT TTAAATTACA AGCATAATAT      1620

TAAATTTTGA ATCAATTAAT TTTTATTTCT ATTATTTTAA TTAATTTAGT CTATTTTTTC      1680

AAAATAAAAT TTAAATCTAA ATAAAAATAA TTTTTCCTTA ATATTATTAA TAAATTTATT      1740

TCAACATCAT ATATTTACTT ATTAATACAT AAATTATAAT AATTTATCAT AATTTTATGG      1800

AAATTGAGAC CAAGAAACAT TAAGAGAACA AATTCTATAA CAAAGACAAT TTAGTAAAAA      1860

TGTACTTTTA GGTAATTTTA AGTACTCTTA ACCAAACACA AAAATTCAAA TCAAATGAAC      1920

CAAATAAGAT AATATAACAT ACAGAATATC CTACTTGTAT TCTTACATTC CCGTAATCAT      1980

ATTATGAAAA GTAATATTAT ATTACCTGAG CCAAATGCTC TCACAAACTA TTATCCAAAA      2040

AAAAAATGTT GAATATAATT TTTATAACAT TTTTTCATAT ATTTGCAAGA TTATATTTTG      2100

TATATTTACG TAAAAATATT TGACATAGAT TGAACACCTT CTTAACATAA TCCCACCATA      2160

AGTCAAGTAT GTAGATGAGA AATTGGTACA AACAACGTGG GGCCAAATCC CACCAAACCA      2220

TCTCTCATCC TCTCCTATAA AAGGCTAGTT ACACATACAC AACAATCCAC ACACAAATAC      2280

ACTCAAAATT CTTTGCTTTG TATTTCGGTT AACCATG                              2317
```

(2) INFORMATION FOR SEQ ID NO:6:

(i) SEQUENCE CHARACTERISTICS:
        (A) LENGTH: 2168 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

```
TTAGAAGAAA AATAGATGTT TTGCGTATAT TGAACTCAAC CATGAAATAC CAACAACAAT        60

ATTTGTATTT TTGGTCCGAC CAAGTGGCAG CCAACATCAA TACTCTACTA TACTTACCAC       120

CAACTGTCCA AGCAACTCAT GTGGGCTTGA ATTGAGACAG AAGCAACTTT ACACCTCTCA       180

TCTATACCAT ATTTGGGTTA AATAAAGTTA TTGCCCAAAA TACAATTTAA TTCAAAAATG       240

GTTAAAATAT ACCATACATT CCTGTATTTT TTTTAAAATT TGAAATTTAG TCCTTATATT       300

TTTATTTCTA GGAATTTAAT CCCTCTACTT TTTAAATCTC AAAATTCATA TCCAACTATT       360

AATACTGTTA GGATTACTTT GTTAAATTCT GGTTCATTTT AATGTCATTT TTGTACCTAC       420

ATTTCTACCA AGTGAGTATT TTTTTTATTT TAAAATGTCA CACTGACAAA TTTAACAAAA       480

AAAATAATGT TAACAATTAA AACGGGATTT TGAAATCTAA AAAGTAAATA AACTAAATTC       540

ATGAGAATAA AAGTATAATG GCTAATTTTT AAATTTGTGA AGAGTACAAG GATCTGTGCC       600

ATATTTTAAC CTTCAAAATT TGATATCTTA CAAAAGTAAA TATTCTTAAT TTAATAGAAT       660

AAAGTTGCTT TATTTTTCTT CAATTCAATA ATAACATATT TCTTTAGAGT TGTTATAACA       720

AGTAAATTAT ATAAAACTAG AGATAGTTTA CACCATAAAA AGTGCATAGA GTCACAAAGA       780

TGAAAGTGGT TCACATTGTA AGTAGTGCAA GGAGCCTAAG AGTGGTGATT TAGCAATGTT       840
```

```
GAGATTGTAT TCGAGTAGAA TATATGCTAT GGTTTCGTAT ATTCTTCTGA GTCTCTCCCT      900

TGCCTTGATG TTGAGGGGGG ATACTTATAA AGGAATGGTG GCAAAACGTG ATTCCCAGCC      960

AGTATGCACT CTACCTCATA TGTGCAAAGG GTAGAGAGGC GAATGTCAGT TTAGAGTGAT     1020

TGCTAGAGTC GATTTAAATG AATGATAAAA TTTCTATAGA AGCTTTAAGA ACCTCAAAAC     1080

CAATACTTTA CGATATTTAT TTTTCTTTAA TTTTTATTTT TTAATTATAT TACATAAGAT     1140

CTGACATGTC ATTTTTTAAC GGTTATATAA CAATTTTAGT AACAAAAGA CCTGATTGAT      1200

ATAACATTAA ATCATCAATA ATTTAAGATG TAATTAGAAT GTTTTAAATT TTAGGGTCAA     1260

TTTAAAATGA GAGTCATAGT TTGAGGATAT CTAATGAAAT TAACATTGTT CTTTAAATTA     1320

AATTTAATAT AATTTATAGA AATAAATTTT ATTTTGGTCG AATTTAGAAC TCTAAGATAA     1380

TTTCCCATTT AACCCATTAA GAAAATTTTA GATTTTGTT ATAGAAGGTG AAGCAGGGAG      1440

GTGTTTAGGT TTTTCAAGAT TAAAGTTATT ATAATTTCAC CTGTGATACA GTTGAAAAAT    1500

CAATTTTCAT ATTTTGGTTG TACATATTCT GTAGAATGTA GTAACATAAT AATAGCTTTT    1560

AAATAAATGG ACAATAATTG CCTTACCGTT AATAACATGG GACAGAAGAA AAAAAGTGTT    1620

TTTGCCTTTG TTGAATCTAA TGAATCCAAG AAAAGAAAAG AGGGTTAAAG AAGAAGGAAG    1680

CAGGGATCAT CAGCTTGGAT CGATCTGCTC ATGGAAATTA AAGCCCCACC CACAGGGAGC    1740

CATCAGCCTC GTTGACATTA GCTGGAAATA GGGCCCAATT TAACCGCCAT CGCTACGGAA    1800

ACTTATTTCC TAAGTTAGCC AAGCATTCGC AATCACAAAC CGAGGCAATC ATTAATTCTT    1860

TTTAATGGTG TTGGATGGTT ATATTATATC TCGATTATAT ATATTTTTT TAAAAACCGA     1920

AGTTGAATGT CTAAATAGGA AGTAATTTTT TTAAATATTAT TTTTTTATAA TATTTGAATC   1980

CGATATCTTA TTTAAAAACC ATCGAAATTT TTATTACTCA ATCATTACCG AAATAGAATC    2040

GGGCTAAAAT ATTTCGAAAA CTAAAAGTTT CACTTTTTAT ATTGAAAAAC GAGGCTTTGT    2100

GATTCTTATA AATTTAATTC ATTGAAATTT CATCAAGTAA AACAGAAGAA TTATAAATCT   2160

CTAAAATG                                                             2168

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:7:

CAGCGGTACC TCGAGCTGGT GGACTGACGC                                       30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:8:

CGGCCTCGAG GTACCTGAAG GAGCATGTTC                                       30
```